(12) United States Patent
Kim et al.

(10) Patent No.: US 10,722,605 B2
(45) Date of Patent: Jul. 28, 2020

(54) PHOTOCATALYST FILTER AND AIR CONDITIONER INCLUDING THE SAME

(71) Applicant: SAMSUNG ELECTRONICS CO., LTD., Suwon-si (KR)

(72) Inventors: Jee-yeon Kim, Seoul (KR); Hee-jin Park, Seoul (KR); Yong-won Jeong, Seoul (KR); Jeong-eun Lee, Seongnam-si (KR); Jun-ho Koh, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 345 days.

(21) Appl. No.: 15/788,352

(22) Filed: Oct. 19, 2017

(65) Prior Publication Data

US 2018/0104374 A1    Apr. 19, 2018

Related U.S. Application Data

(60) Provisional application No. 62/410,052, filed on Oct. 19, 2016.

(30) Foreign Application Priority Data

Sep. 1, 2017    (KR) ......................... 10-2017-0112112

(51) Int. Cl.
*B01D 53/02*    (2006.01)
*A61L 9/20*    (2006.01)
(Continued)

(52) U.S. Cl.
CPC ............ *A61L 9/205* (2013.01); *B01D 53/007* (2013.01); *B01D 53/04* (2013.01);
(Continued)

(58) Field of Classification Search
CPC ... A61L 9/00; A61L 9/20; A61L 9/205; A61L 2209/111; A61L 2209/16; A61L 2209/12;
(Continued)

(56) References Cited

U.S. PATENT DOCUMENTS 8,740,420 B2    6/2014    Nishioka et al.
9,011,780 B1    4/2015    Burnett
(Continued)

FOREIGN PATENT DOCUMENTS

EP    1112752 A2    7/2001
EP    1 574 225 A1    9/2005
(Continued)

OTHER PUBLICATIONS

Communication dated Aug. 2, 2019, issued by the European Patent Office in counterpart European Application No. 17861388.1.
(Continued)

*Primary Examiner* — Monzer R Chorbaji
(74) *Attorney, Agent, or Firm* — Sughrue Mion, PLLC

(57) ABSTRACT

A photocatalyst filter is provided. The photocatalyst filter includes: a base in which an internal space is formed. The internal space is permeable to fluid, and a plurality of photocatalyst beads are provided in the internal space, wherein a surface of the internal space is reflective.

14 Claims, 35 Drawing Sheets

(51) Int. Cl.
  *B01D 53/86* (2006.01)
  *B01D 53/30* (2006.01)
  *F24F 3/16* (2006.01)
  *B01D 53/00* (2006.01)
  *B01D 53/04* (2006.01)
  *B01J 20/16* (2006.01)
  *B01J 20/20* (2006.01)
  *B01J 35/00* (2006.01)
  *B01J 35/08* (2006.01)

(52) U.S. Cl.
  CPC ......... *B01D 53/0454* (2013.01); *B01D 53/30* (2013.01); *B01D 53/8625* (2013.01); *B01D 53/8634* (2013.01); *B01D 53/8668* (2013.01); *B01D 53/8671* (2013.01); *B01D 53/8696* (2013.01); *B01J 20/16* (2013.01); *B01J 20/20* (2013.01); *B01J 35/004* (2013.01); *B01J 35/08* (2013.01); *F24F 3/1603* (2013.01); *A61L 2209/111* (2013.01); *A61L 2209/12* (2013.01); *A61L 2209/14* (2013.01); *A61L 2209/16* (2013.01); *A61L 2209/22* (2013.01); *B01D 2253/102* (2013.01); *B01D 2253/108* (2013.01); *B01D 2253/34* (2013.01); *B01D 2255/20707* (2013.01); *B01D 2255/802* (2013.01); *B01D 2257/302* (2013.01); *B01D 2257/404* (2013.01); *B01D 2257/702* (2013.01); *B01D 2257/90* (2013.01); *B01D 2257/91* (2013.01); *B01D 2258/06* (2013.01); *B01D 2259/4508* (2013.01); *B01D 2259/802* (2013.01); *B01D 2259/804* (2013.01); *C02F 2305/10* (2013.01); *F24F 2003/1628* (2013.01)

(58) Field of Classification Search
  CPC ....... B01J 20/20; B01J 19/123; B01D 53/007; F24F 3/1603
  USPC ......................................... 422/5; 96/108, 224
  See application file for complete search history.

(56) References Cited

U.S. PATENT DOCUMENTS

| | | | |
|---|---|---|---|
| 2001/0052237 A1* | 12/2001 | Saitou | A61L 9/205 62/264 |
| 2005/0063881 A1 | 3/2005 | Senne et al. | |
| 2005/0201907 A1 | 9/2005 | Wakamura | |
| 2015/0306533 A1 | 10/2015 | Matlin et al. | |
| 2016/0121265 A1 | 5/2016 | Kanda et al. | |

FOREIGN PATENT DOCUMENTS

| | | |
|---|---|---|
| JP | 2001-293072 A | 10/2001 |
| JP | 2005-177226 A | 7/2005 |
| JP | 2008-245693 A | 10/2008 |
| JP | 2009-247546 A | 10/2009 |
| JP | 2015-62640 A | 4/2015 |
| KR | 10-0541026 B1 | 1/2006 |
| WO | 2005/099778 A1 | 10/2005 |
| WO | 2011135601 A1 | 11/2011 |

OTHER PUBLICATIONS

Ren, H., et al., "Photocatalytic materials and technologies for air purification", Aug. 31, 2016, Journal of Hazardous Materials, vol. 325, p. 340-366, 27 pages total.

Lazar, M., et al., "Photocatalytic Water Treatment by Titanium Dioxide: Recent Updates", Dec. 19, 2012, Catalysts, vol. 2, No. 4, p. 572-601, 31 pages total.

International Search Report (PCT/ISA/210), issued by International Searching Authority in corresponding International Application No. PCT/KR2017/011600 dated Feb. 13, 2018.

Written Opinion issued (PCT/ISA/237) by the International Searching Authority in corresponding International Application No. PCT/KR2017/011600 dated Feb. 13, 2018.

Communication dated Nov. 11, 2019, issued by the European Patent Office in counterpart European Application No. 17861388.1.

* cited by examiner

SACRIFICIAL CORE.    $TiO_2$ COATING    CALCINATION (~500°C) OR
(ex. $SiO_2$, $CaCO_3$, POLYSTYRENE...)      CALCINATIONS
                                                             + ACID/BASE ETCHING

210

"PUT ORANGE PHOTOCATALYST BEADS BY TWO SPOONS"

FIG. 22A    FIG. 22B    FIG. 22C
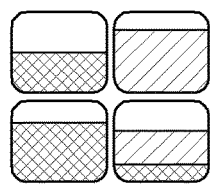 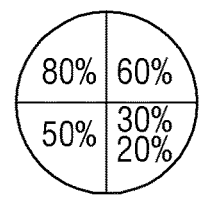 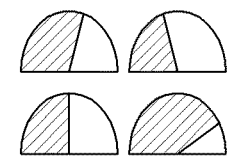
FIG. 22D    FIG. 22E
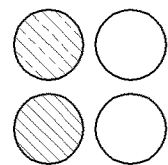 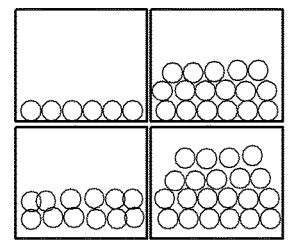

FIG. 23A  FIG. 23B  FIG. 23C
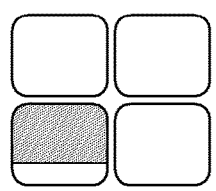 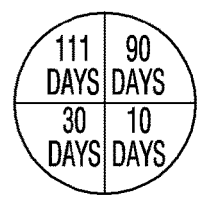 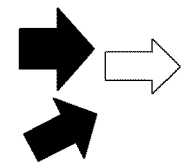
FIG. 23D  FIG. 23E
CURRENT STEP
(FILTER 1 DECOMPOSITION)
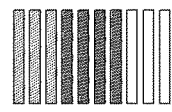
CURRENT STEP
(SENSOR IS BEING OPERATED)
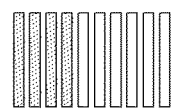
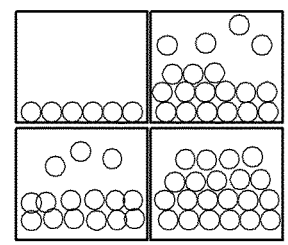

PHOTOCATALYST FILTER AND AIR CONDITIONER INCLUDING THE SAME

CROSS-REFERENCE TO RELATED APPLICATIONS

This application claims the benefit of Korean Patent Application No. 10-2017-0112112, filed on Sep. 1, 2017, in the Korean Intellectual Property Office, and U.S. Provisional Patent Application No. 62/410,052, filed on Oct. 19, 2016, in the USPTO, the disclosures of which are incorporated herein by reference in their entireties.

BACKGROUND

Field of the Invention

Apparatuses consistent with exemplary embodiments relate to a photocatalyst filter and an air conditioner including the same, and more particularly, to a photocatalyst filter having an increased light efficiency due to the use of light reflecting structures, and an air conditioner including the same.

Description of the Related Art

Recently, in accordance with an increase in a demand for air purifiers for indoor use for filtering air pollution, fine dust, yellow dust, and the like, various types of air purifiers have been produced. For example, related art air purifiers may use filters including non-woven fabrics, an electrical dust collection type electrostatic filter, or other type of filter. However, such filters filter dust, but it is difficult for such filters to remove odors or to sterilize bacteria. Therefore, separate deodorizing filters using activated carbon are used for the purpose of deodorization. However, such deodorizing filters of activated carbon are not durable, and may not sterilize harmful microorganisms present in the air.

To solve these problems, studies are being done on the use of photocatalyst materials that may perform deodorization, sterilization, and the like, and a typical example of such a photocatalyst material is titanium dioxide ($TiO_2$). Titanium dioxide generates radicals when irradiated with infrared light, and may thereby sterilize microorganisms and decompose odor-causing particles by the strong oxidizing power of such radicals.

To use the photocatalyst material as described above, separate light sources such as light emitting diodes (LEDs) are typically included in the air purifier. As a number of light sources is increased, the photocatalyst reaction is increased, such that the an air purifying effect may be increased, but the energy consumed also increases.

Therefore, there is a demand for an air purifier utilizing a photocatalyst that may improve air purification while reducing energy consumption.

SUMMARY OF THE INVENTION

Exemplary embodiments of the present disclosure may overcome the above disadvantages and other disadvantages not described above. Also, the present disclosure is not required to overcome the disadvantages described above, and an exemplary embodiment of the present disclosure may not overcome any of the problems described above.

Exemplary embodiments may provide a photocatalyst filter utilizing with increased light reflecting structures for increased light efficiency, and an air conditioner including the same.

According to an aspect of an exemplary embodiment, a photocatalyst filter includes: a base in which an internal space, permeable to a fluid passes; and a plurality of photocatalyst beads provided in the internal space, wherein a surface of the internal space has a light reflectivity.

The internal space may be defined by a plurality of walls in the base, and all of the plurality of walls may have a light reflectivity.

The plurality of walls may be formed of a reflective material.

The reflective material may be a metal or a light-reflective resin.

The plurality of photocatalyst beads may include photocatalyst materials and adsorbents.

The adsorbent may be at least one of activated carbon and zeolite.

The plurality of photocatalyst beads may have spherical shapes that are hollow.

The plurality of photocatalyst beads may have protrusions formed on surfaces thereof.

The photocatalyst filter may further include a cover attached to the base so that the photocatalyst beads are retained within the base, wherein the cover includes a photocatalyst material.

According to an aspect of another exemplary embodiment, an air conditioner includes: a photocatalyst filter including a base in which an internal space, permeable to fluid, is formed and a plurality of photocatalyst beads provided in the internal space, a surface of the internal space having a light reflectivity; a fan unit configured to introduce air into the photocatalyst filter; a light source portion configured to irradiate light onto the photocatalyst filter; and a processor configured to control the fan unit and the light source portion.

The air conditioner may further include a second photocatalyst filter including a plurality of photocatalyst beads, wherein the fan unit includes: a first fan configured to introduce the air into the photocatalyst filter; and a second fan configured to introduce the air into the second photocatalyst filter.

The photocatalyst beads included in the photocatalyst filter and the photocatalyst beads included in the second photocatalyst filter may be different in at least one of sizes, shapes, and components from each other.

The air conditioner may further include a sensor configured to sense a harmful material, wherein the processor is configured to individually control the first fan and the second fan depending on a result sensed by the sensor.

The air conditioner may further include a second photocatalyst filter configured to include a plurality of photocatalyst beads, wherein the light source portion includes: a first light source configured to irradiate the light onto the photocatalyst filter; and a second light source configured to irradiate the light onto the second photocatalyst filter.

The air conditioner may further include a sensor configured to sense a harmful material, wherein the processor is configured to individually control the first light source and the second light source depending on a result sensed by the sensor.

BRIEF DESCRIPTION OF THE DRAWING FIGURES

The above and/or other exemplary aspects and advantages o will be more apparent by describing certain exemplary embodiments of the present disclosure with reference to the accompanying drawings, in which.

Figure 18:
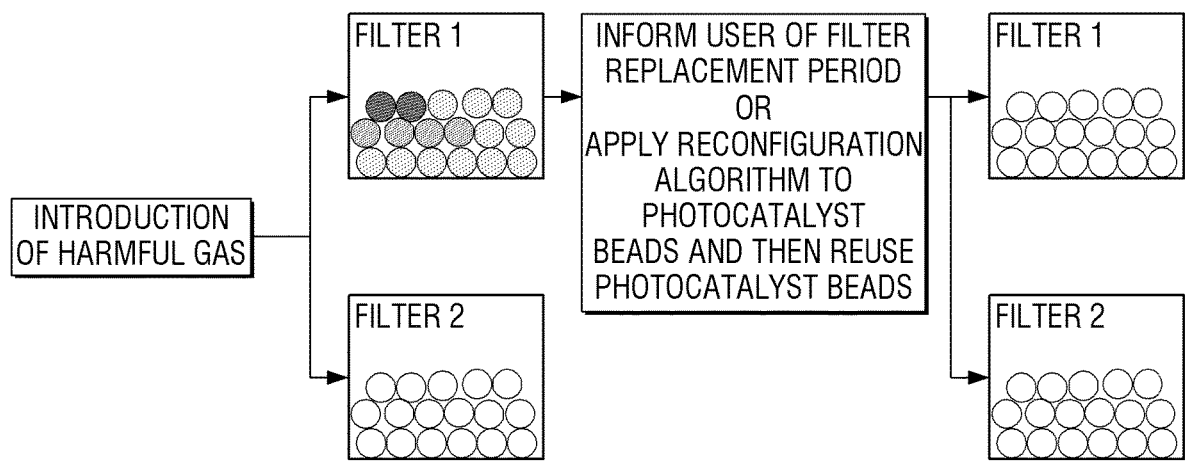
Figure 19:
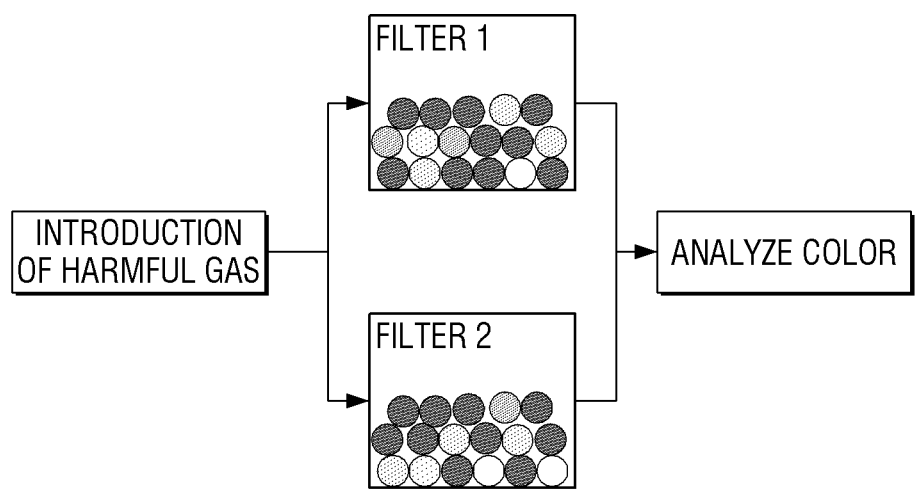
Figure 25:
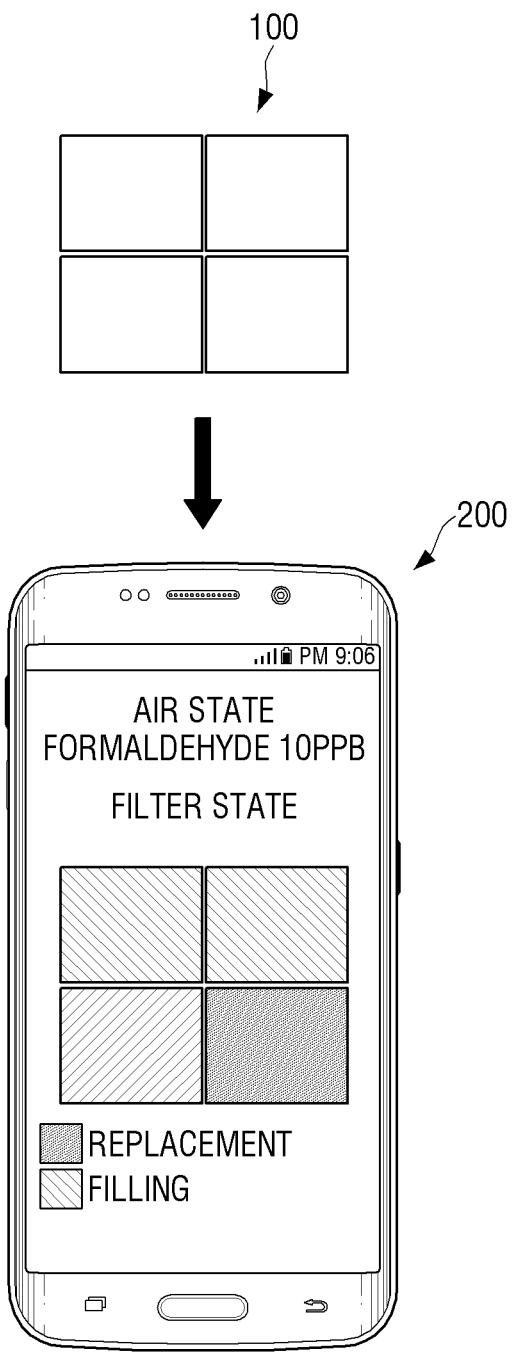
Figure 26:
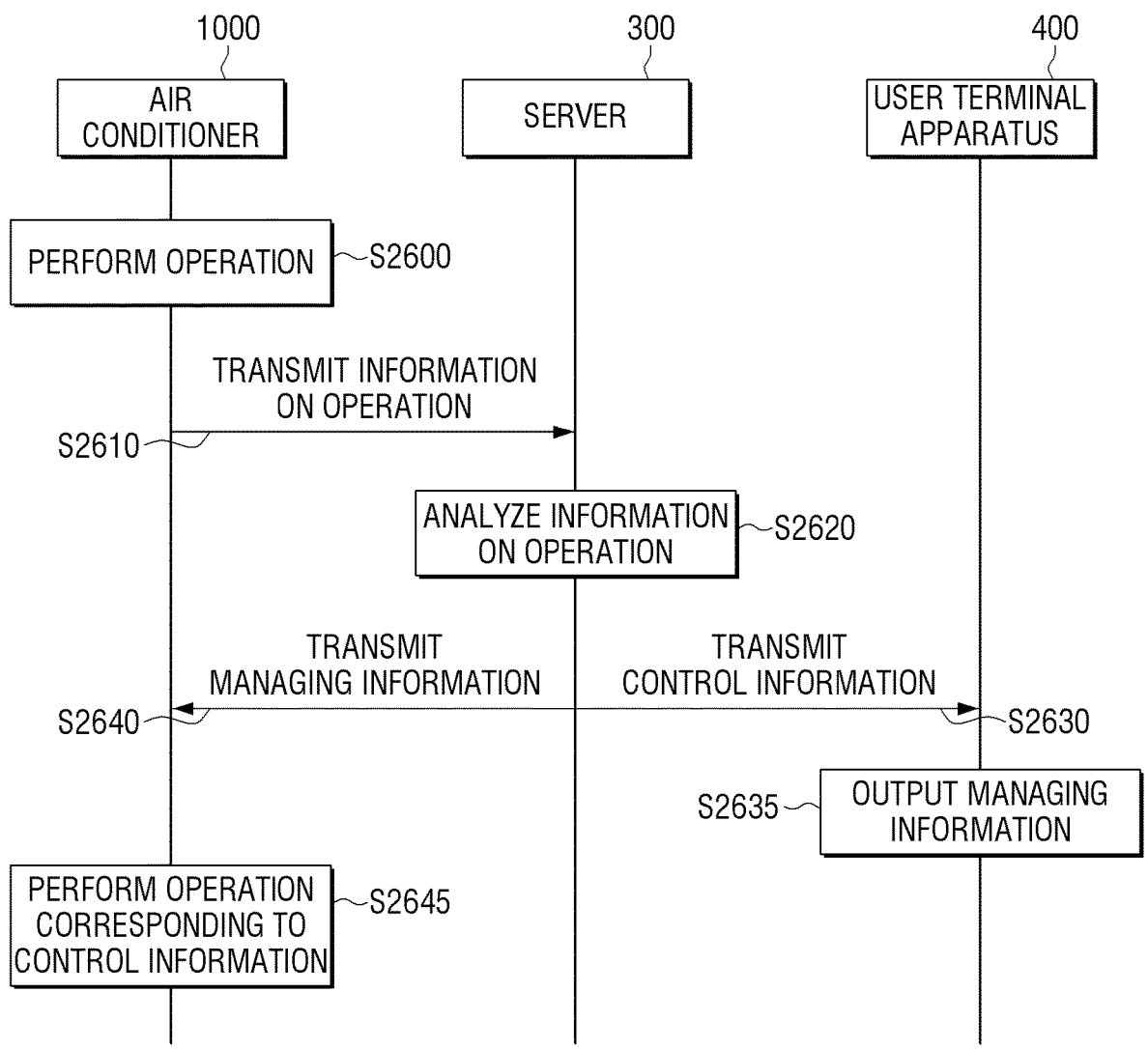
Figure 27:
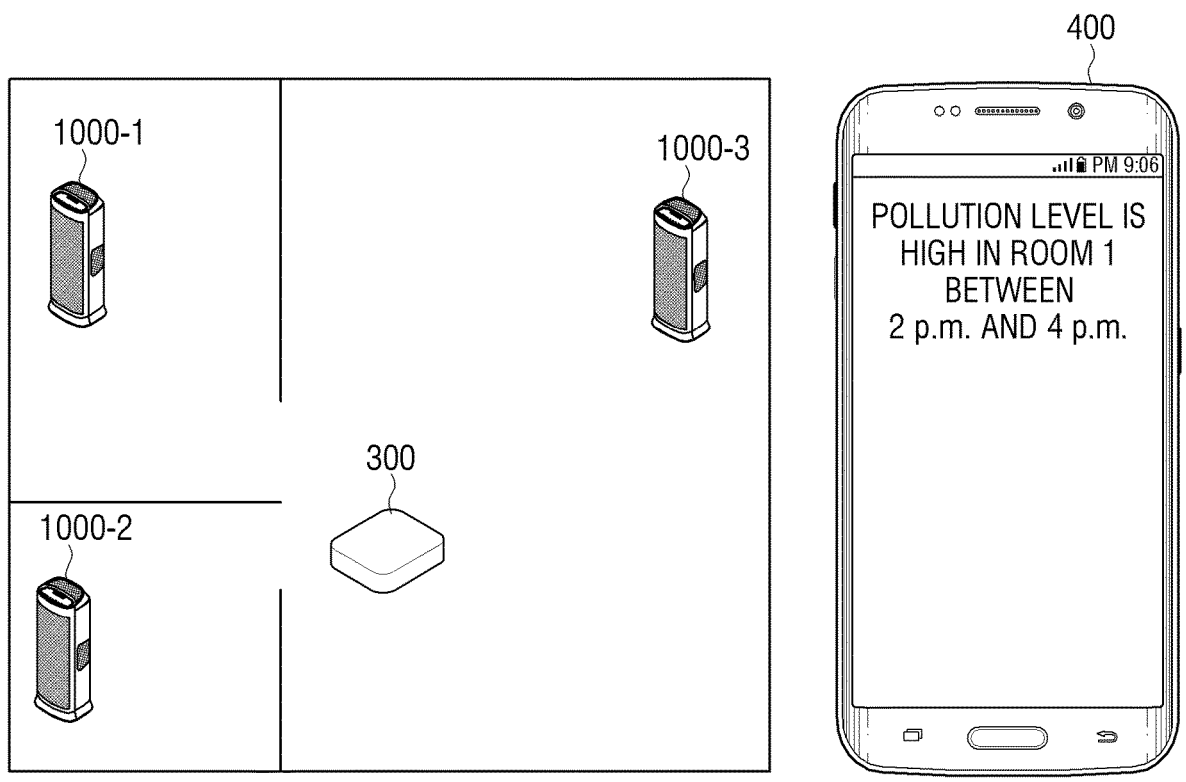

FIGS. 16(*a*), 16(*b*), 16(*c*), and 16(*d*) are views for describing a method of providing information on pollution levels on a photocatalyst filter according to diverse exemplary embodiments of the present disclosure;

FIGS. 17(*a*), 17(*b*), 17(*c*), and 17(*d*) are views for describing a method of providing information on pollution levels on a photocatalyst filter according to diverse exemplary embodiments of the present disclosure;

FIG. 18 is a view for describing a filter replacement period informing manner according to an exemplary embodiment of the present disclosure;

FIG. 19 is a view for describing a gas analyzing manner according to an exemplary embodiment of the present disclosure;

FIGS. 20(*a*), 20(*b*), 20(*c*), and 20(*d*) are views for describing a method of providing information on packing factors of photocatalyst beads according to diverse exemplary embodiments of the present disclosure;

FIGS. 21(*a*) and 21(*b*) are views for describing a method of providing information on a manner of filling photocatalyst beads according to an exemplary embodiment of the present disclosure;

FIGS. 22(*a*), 22(*b*), 22(*c*), 22(*d*), and 22(*e*) are views for describing a method of providing information on packing factors of photocatalyst beads according to diverse exemplary embodiments of the present disclosure;

FIGS. 23(*a*), 23(*b*), 23(*c*), 23(*d*), and 23(*e*) are views for describing a method of providing information on an operation progress situation of a photocatalyst filter according to an exemplary embodiment of the present disclosure;

FIGS. 24(*a*), 24(*b*), 24(*c*), and 24(*d*) are views for describing a method of providing information on states in the respective spaces in a photocatalyst filter according to diverse exemplary embodiments of the present disclosure;

FIG. 25 is a view for describing a method of providing information on states in the respective spaces in a photocatalyst filter according to diverse exemplary embodiments of the present disclosure; and FIGS. 26 and 27 are views for describing diverse exemplary embodiments of the present disclosure for an air conditioner and a server.

DETAILED DESCRIPTION OF THE EXEMPLARY EMBODIMENTS

The exemplary embodiments of the present disclosure may be diversely modified. Accordingly, specific exemplary embodiments are illustrated in the drawings and are described in detail in the detailed description. However, it is to be understood that the present disclosure is not limited to a specific exemplary embodiment, but includes all modifications, equivalents, and substitutions without departing from the scope and spirit of the present disclosure. Also, well-known functions or constructions are not described in detail since they would obscure the disclosure with unnecessary detail.

The terms "first", "second", etc. may be used to describe diverse components, but the components are not limited by the terms. The terms are only used to distinguish one component from the others.

The terms used in the present application are only used to describe the exemplary embodiments, but are not intended to limit the scope of the disclosure. The singular expression also includes the plural meaning as long as it does not differently mean in the context. In the present application, the terms "include" and "consist of" designate the presence of features, numbers, steps, operations, components, elements, or a combination thereof that are written in the specification, but do not exclude the presence or possibility of addition of one or more other features, numbers, steps, operations, components, elements, or a combination thereof.

In the exemplary embodiment of the present disclosure, a "module" or a "unit" performs at least one function or operation, and may be implemented with hardware, software, or a combination of hardware and software. In addition, a plurality of "modules" or a plurality of "units" may be integrated into at least one module except for a "module" or a "unit" which has to be implemented with specific hardware, and may be implemented with at least one processor (not shown).

Hereinafter, the present disclosure will be described in detail with reference to the accompanying drawings.

Figure 1:
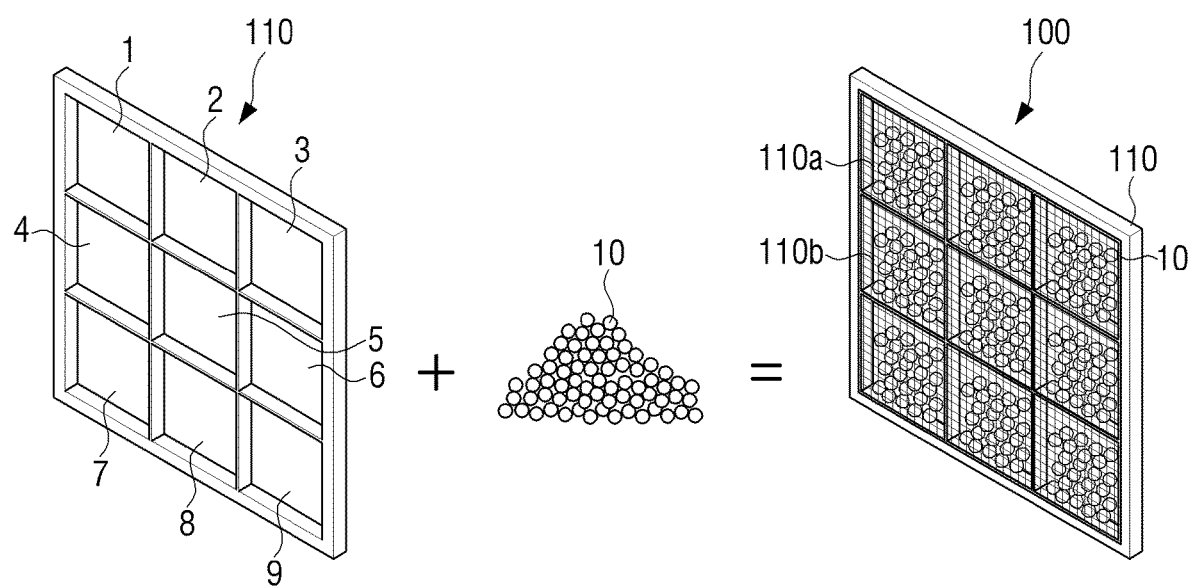
FIGS. 1 and 2 are views for describing a photocatalyst filter according to diverse exemplary embodiments of the present disclosure.

FIG. 1 is a view for describing a photocatalyst filter according to an exemplary embodiment of the present disclosure.

Referring to FIG. 1, a photocatalyst filter 100 includes a base 110 in which one or more internal spaces 1 to 9 are formed. Fluid may flow through the internal spaces, and photocatalyst beads 10 provided in one or more of the internal spaces 1 to 9.

The photocatalyst filter 100 may perform an antibacterial function, an atmosphere purifying function, a deodorizing function, an antifouling function, and a water purifying function using a photocatalyst material. For example, the photocatalyst filter 100 may sterilize various pathogens and bacteria, remove harmful materials such as a nitrogen oxide (NOx), a sulfur oxide (SOx), formaldehyde, and the like, from the air, decompose odor materials such as acetaldehyde, ammonia, a hydrogen sulfide, and the like, decompose harmful materials such as cigarette smoke, oil residues, and the like, and decompose harmful organic compounds of wastewater.

The one or more internal spaces 1 to 9 of the photocatalyst filter 100 are defined by a plurality of walls within in the base 110.

FIG. 1 illustrates the photocatalyst filter 100 including internal spaces 1 to 9, each having a quadrangular shape. Internal spaces 1 to 9 are each defined by four walls, and are each filled with photocatalyst beads 10.

The internal spaces 1 to 9 of the photocatalyst filter 100 may have various shapes, for example, the quadrangular shape as illustrated in FIG. 1, a honeycomb structure, another polygonal structure, or a circular shape. As an example, a photocatalyst filter including internal spaces having a honeycomb structure is illustrated in FIG. 2.

Figure 2:
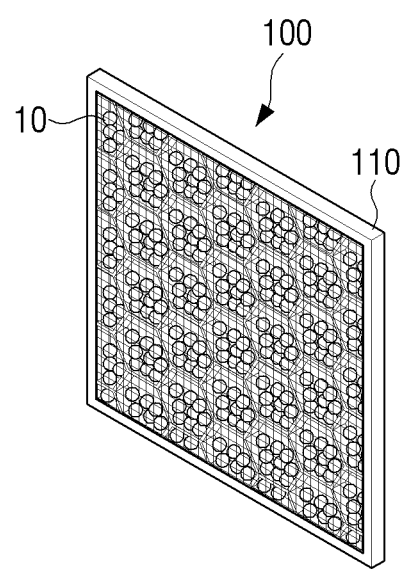

Referring to FIG. 2, the base 110 of the photocatalyst filter 100 may include a plurality of internal spaces having a honeycomb structure with six walls, and the photocatalyst beads 10 are filled in the respective spaces.

Referring to FIG. 1, covers having air permeability may be disposed on a front surface and a rear surface of the photocatalyst filter 100 to hold the photocatalyst beads 10 within the internal spaces of the photocatalyst filter 100. The covers may have a net structure. The covers 110a and 110b may be adhered and fixed to at least one of the walls defining the internal spaces. Since adhesion between the walls and the covers 110a and 110b may become weak over time, the cover 110a, disposed on the front surface of the photocatalyst filter 100, and the cover 110b, disposed on the rear surface of the photocatalyst filter 100, may be adhered to each other such that they are in contact with each other in regions in which the photocatalyst beads 10 are not filled, thereby to strongly fixing the covers 110a and 110b.

The same kind of photocatalyst beads or different kinds of photocatalyst beads may be filled in each of the internal spaces provided in the photocatalyst filter 100. Here, the different kinds mean that photocatalyst materials configuring the photocatalyst beads are different from one another or shapes, sizes, and the like, of the photocatalyst beads are different from one another. The shapes and the sizes of the photocatalyst beads may be appropriately selected depending on a kind, a removal rate, and a removal speed of gas to be removed. The respective internal spaces in the photocatalyst filter 100 may be configured to remove different gases, and may have different removal rates and removal speeds. Therefore, the kinds of photocatalyst beads filled in the respective internal spaces, for example, sizes, shapes, materials, and the like, of the photocatalyst beads may be different from one another. That is, for example, the kinds of photocatalyst beads filled in the first internal space 1 and the second internal space 2 may be different from each other. In addition, different kinds of photocatalyst beads may also exist within the same internal space. In addition, the numbers of photocatalyst beads filled in each of the internal spaces provided in the photocatalyst filter 100 may be the same as or different from one another.

The photocatalyst filter illustrated in FIGS. 1 and 2 is only an example, and may include internal spaces having various structures. In addition, the number of internal spaces configuring the photocatalyst filter 100 is not limited to that illustrated in FIGS. 1 and 2. In addition, the photocatalyst filter 100 does not necessarily include the plurality of internal spaces, but may also include only a single internal space.

The photocatalyst beads filled in the photocatalyst filter 100 may be formed of a photocatalyst material itself or be formed of a photocatalyst material and another additional material. For example, the photocatalyst bead 10 may include the photocatalyst material and an adsorbent (for example, activated carbon, zeolite, sepiolite, $SiO_2$, clay, or the like) that may better adsorb impurities. The photocatalyst bead may have a spherical shape, a cylindrical shape, a hexahedral shape, a porous shape, or the like, and are not limited to having a specific shape, but may have any shape, may have a smooth surface, and may have a protrusion formed on a surface thereof to increase a reaction surface area. In addition, a size of the photocatalyst bead may be an average diameter of, for example, 0.5 to 4 mm. However, a size of the photocatalyst bead is not limited thereto, but may be determined in consideration of various features such as a reaction surface area, the size of the photocatalyst filter 100, and the like. In addition, the numbers of photocatalyst beads filled in the respective internal spaces of the photocatalyst filter 100 may be various, and may be different from one another. In addition, a mass of the photocatalyst bead may be, for example, 500 to 1000 g.

The terms "photocatalyst particle," "photocatalyst pellet," or other terms may be used to refer to the photocatalyst beads.

An example of the photocatalyst material configuring the photocatalyst bead may include titanium oxide ($TiO_2$), zinc oxide (ZnO), cadmium sulfide (CdS), tungsten oxide ($WO_3$), vanadium oxide ($V_2O_3$), and the like, but is not limited thereto.

Figure 3A:
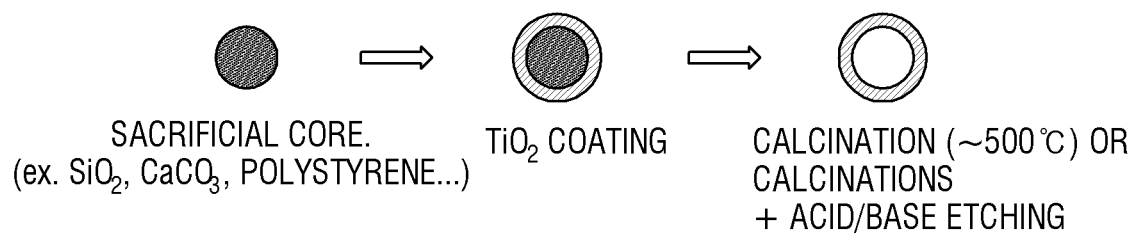
FIGS. 3A and 3B are views for describing methods of manufacturing photocatalyst beads according to diverse exemplary embodiments of the present disclosure.
Figure 3B:
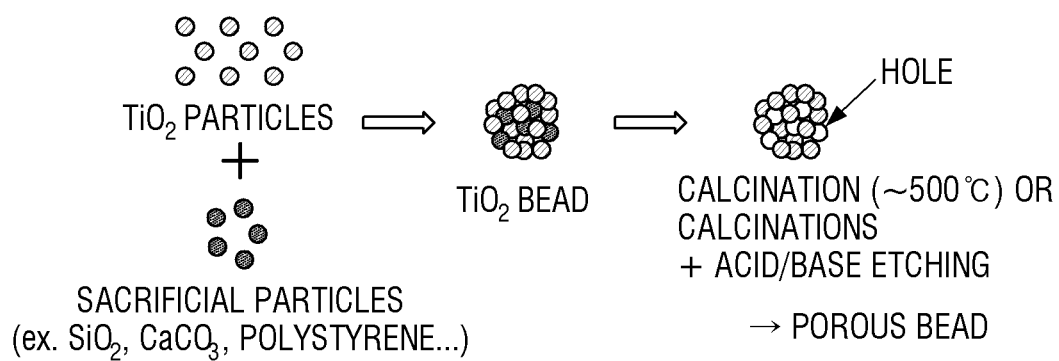

FIGS. 3A and 3B are views for describing various forms of a photocatalyst bead.

FIG. 3A is a view for describing a method of manufacturing photocatalyst beads that are hollow according to an exemplary embodiment of the present disclosure.

Referring to FIG. 3A, photocatalyst beads that are hollow and have a spherical shape may be manufactured by coating surfaces of sacrificial cores with a photocatalyst material and then calcinating internal particles or removing the internal particles through acid/base etching, or the like.

The internal particle may be any particle that may be easily removed. For example, $SiO_2$, $CaCO_3$, polystyrene, or the like, may be used.

An example of the photocatalyst material coating the internal particle may include titanium oxide ($TiO_2$), zinc oxide (ZnO), cadmium sulfide (CdS), tungsten oxide ($WO_3$), vanadium oxide ($V_2O_3$), and the like, but is not limited thereto.

Since the photocatalyst beads that are hollow and have the spherical shape as described above have a low density, when air is introduced, the photocatalyst beads may freely move in the internal space of the photocatalyst filter 100, and contact areas between the photocatalyst beads and the air may thus be increased.

FIG. 3B is a view for describing a method of manufacturing photocatalyst beads 10 having another form.

Referring to FIG. 3B, when sacrificial particles are mixed with photocatalyst particles to generate intermediate particles and the sacrificial particles are removed from the intermediate particles through calcination, acid/base etching, or the like, photocatalyst beads including spaces, in which the sacrificial particles have been removed, to have wide surface areas may be manufactured.

A material that may be used as the sacrificial particles may be any material that may be easily removed. For example, $SiO_2$, $CaCO_3$, polystyrene, or the like, may be used.

An example of a material that may be used as the photocatalyst particles mixed with the sacrificial particles may include titanium oxide ($TiO_2$), zinc oxide (ZnO), cadmium sulfide (CdS), tungsten oxide (WO$_3$), vanadium oxide (V$_2$O$_3$), and the like, but is not limited thereto.

Since the photocatalyst beads manufactured according to the present method have an uneven surface and have a plurality of spaces therein, contact areas between the photocatalyst beads and air may be increased. When the photocatalyst beads having the increased contact areas with the air are used, a larger number of photocatalyst reactions may occur, and filter efficiency may thus be increased. The forms described with reference to FIGS. 3A and 3B are only an example, and exemplary embodiments are not limited thereto.

In addition to the methods of manufacturing the photocatalyst beads described above, the photocatalyst beads may also be manufactured by kneading, binding, and adsorbing materials or be manufactured in a uniform shape using a mold having a specific shape.

According to another exemplary embodiment of the present disclosure, the base 110 itself, within which the photocatalyst beads 10 are accommodated, as well as the photocatalyst beads 10 may include a photocatalyst material, and the covers 110a and 110b may also include a photocatalyst material. As an example, the base 110 itself may be formed of the photocatalyst material or a form of the base 110 may be completed using another material and may then be coated with the photocatalyst material. In addition, the covers 110a and 110b themselves may be formed of the photocatalyst material or forms of the covers 110a and 110b may be completed using another material and may then be coated with the photocatalyst material.

The photocatalyst materials included in the photocatalyst beads 10, the base 110, and the covers 110a and 110b of the photocatalyst filter 100 may react to light to remove harmful gases, odor materials, microorganisms, and the like. To efficiently utilize light, according to an exemplary embodiment of the present disclosure, the photocatalyst filter 100 may include a component for reflecting the light. This will be described with reference to FIG. 4.

Figure 4:
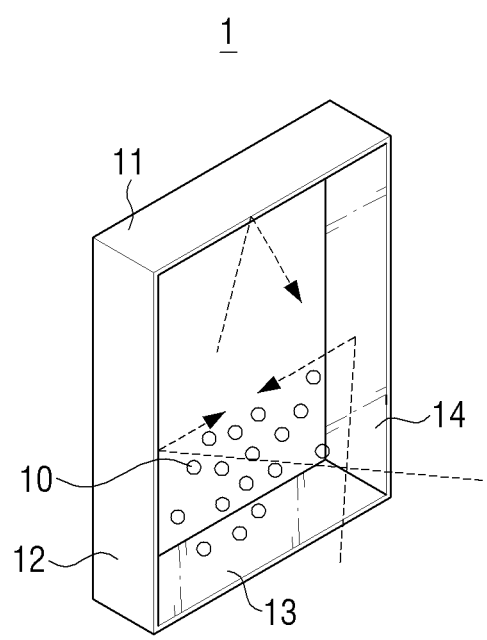
FIG. 4 is a view for describing light reflection in a photocatalyst filter according to an exemplary embodiment of the present disclosure.

FIG. 4 is a side view illustrating only the first internal space 1 of the plurality of internal spaces configuring the photocatalyst filter 100 described with reference to FIG. 1.

Referring to FIG. 4, the first internal space 1 includes first to fourth walls 11 to 14. Some or all of the first to fourth walls 11 to 14 have a light reflectivity. For example, a surface of at least one of the first to fourth walls 11 to 14 may include a material having a high light reflectivity, for example, a metal such as aluminum, silver, platinum, or the like, a light-reflective resin, a glass, a nano-metal, or the like. In this case, the first to fourth walls 11 to 14 themselves may be formed of the material having the high reflectivity or a base material of the first to fourth walls 11 to 14 may be a material of which a reflectivity is not high and may be coated with the material having the high reflectivity. Only inner portions of the first to fourth walls 11 to 14 may be formed of the material having the high reflectivity or outer portions of the first to fourth walls 11 to 14 may also be formed of the material having the high reflectivity.

Dotted lines illustrated in FIG. 4 indicate light paths, and, as shown, light may be reflected from at least one of the first to fourth walls 11 to 14 and then be incident on the photocatalyst beads 10.

Although the photocatalyst filter having internal spaces with quadrangular structures is described by way of example in FIG. 4, surfaces of walls defining the internal spaces may have a light reflectivity, as described above with reference to FIG. 4, also in the photocatalyst filter having the internal spaces with the honeycomb structure of FIG. 2 or a photocatalyst filter having internal spaces with another form.

In addition, at least one of the cover 110a disposed on the front surface of the photocatalyst filter 100 and the cover 110b disposed on the rear surface of the photocatalyst filter 100 may contain a material having a high reflectivity.

Since the photocatalyst filter 100 includes the component for reflecting the light as described above, an amount of light arriving at the photocatalyst beads 10 may be increased. That is, light efficiency may be increased.

The component for reflecting the light may also be disposed in another portion of the photocatalyst filter 100. An exemplary embodiment of the present disclosure related to this will be described with reference to FIG. 5.

Figure 5:
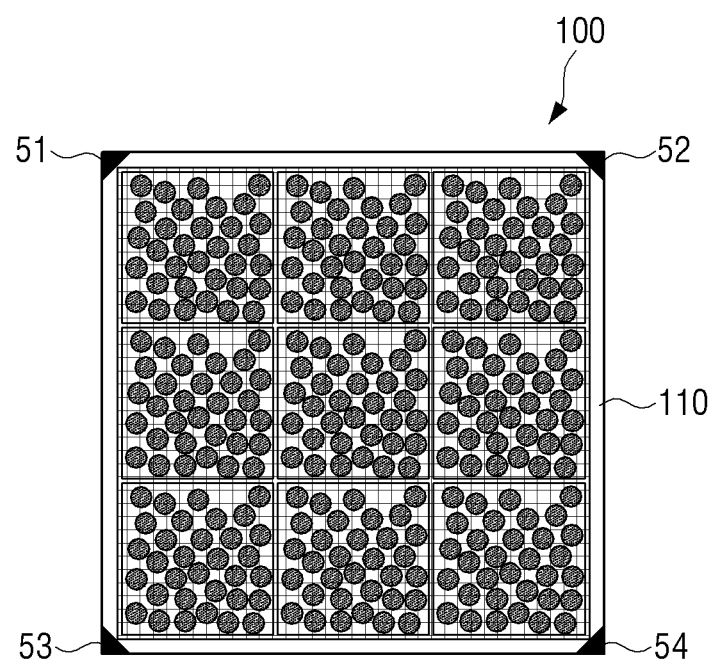
FIG. 5 is a view for describing light reflecting structures in the photocatalyst filter according to an exemplary embodiment of the present disclosure.

FIG. 5 illustrates a photocatalyst filter 100 according to another exemplary embodiment of the present disclosure, and the photocatalyst filter 100 may include light reflecting structures 51 to 54 disposed at corners of a base 110. Although a case in which the light reflecting structures 51 to 54 are disposed in all the corners is illustrated in FIG. 5, the light reflecting structures 51 to 54 may also be disposed in only some of the corners.

According to an exemplary embodiment, the light reflecting structures 51 to 54 may be micro electro mechanical systems (MEMS) mirrors of which angles may be adjusted. Surfaces of the light reflecting structures 51 to 54 may include, for example, a material having a light high reflectivity (for example, a metal such as aluminum, silver, platinum, or the like, a glass, a nano-metal, or the like).

Although a case in which the light reflecting structures are disposed in only the corner of the photocatalyst filter 100 is illustrated in FIG. 5, the light reflecting structures may also be disposed at edges of the photocatalyst filter 100. The more the light reflecting structures, the higher the light efficiency.

Since a photocatalyst filter 100 according to exemplary embodiments may perform the antibacterial function, the atmosphere purifying function, the deodorizing function, the antifouling function, and the water purifying function using the photocatalyst material as described above, the present disclosure may be utilized in any of various fields. For example, the photocatalyst filter 100 may be disposed in a refrigerator, a Kimchi refrigerator, a closet, a shoe rack, a washing machine, a water-purifier tank, a sterilizer, a humidifier, a cleaner, an air conditioning device, an air conditioner, or the like, to perform functions such as a deodorizing function, a water purifying function, a sterilizing function, an air purifying function, and the like. In addition, the photocatalyst filter 100 may also be used in a small product. For example, the photocatalyst filter 100 may be disposed in a smart phone, a tablet personal computer (PC), a smart watch, a patch, or other products (for example, gloves, a band, a necklace, a bracelet, a ring, a headband, an earphone, an earring, clothing, and the like). In addition, the photocatalyst filter 100 may also be used in a window frame, wallpaper, a construction, an air conditioning system, a bathroom tile, or the like. The areas, numbers, materials, and the like, of photocatalyst beads may be different from one another depending on the fields to which the photocatalyst filter is applied. For example, when the photocatalyst filters are to be disposed in a refrigerator, the areas, numbers, materials, and the like, of the photocatalyst filters may be different from one another depending on a kind of food stored in the refrigerator. In addition, photocatalyst filters to be used in a washing machine may be formed of a material to which a hydrophilic material may be bound, and photocatalyst filters to be used in a sterilizer may be formed of a material to which a sterilizing material may be bound. Photocatalyst filters to be applied to a band may include an attachable material that may be simply attached, and the numbers of photocatalyst filters may be various depending on areas in which they are used. Further, photocatalyst filters applied to wallpaper may be formed of a material to which a deodorizing material may be bound, and areas and the numbers of photocatalyst filters may be various.

An example in which the photocatalyst filter 100 is installed in an air conditioner, from among the various applications described above, will hereinafter be described.

Figure 6:
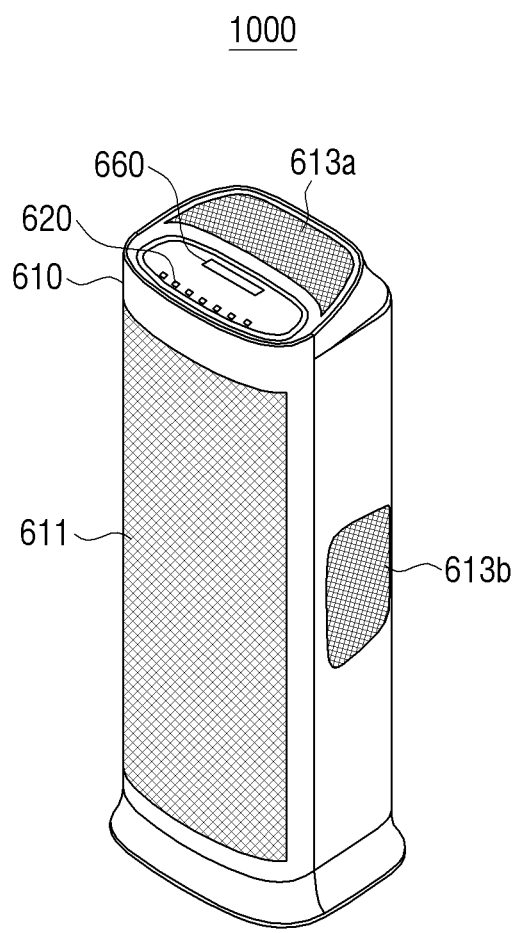
FIG. 6 is a view illustrating an air conditioner according to an exemplary embodiment of the present disclosure.

FIG. 6 is a view for describing an air conditioner 1000 according to an exemplary embodiment of the present disclosure.

Referring to FIG. 6, the air conditioner 1000 may include a body 610, providing the outer appearance of the air conditioner, an inlet 611 for sucking air from a space external to the air conditioner into the air conditioner, outlets 613a and 613b for discharging the sucked and purified air, an input unit 620, and a display unit 600 for displaying an operation state of the air conditioner 1000.

The term "air conditioner" is used herein to refer to any and all types of devices having the function of cleaning air. For example, the air conditioner 1000 may be implemented by an air purifier, an air conditioning device, a humidifier, or the like.

The input unit 620 may include buttons for inputting various control information related to the air conditioner 1000, such as a power button for turning on or off the air conditioner 1000, a timer button for setting a driving time of the air conditioner 1000, a locking button for limiting a manipulation of the input unit to prevent an erroneous manipulation of the input unit, and the like. Here, the respective input buttons may be push switches or membrane switches generating input signals through pressurization of a user or touch switches generating input signals through a touch of a part of a user's body.

In the case in which the input unit 620 uses a touch switch manner, the input unit 620 and the display unit 660 may also be implemented integrally with each other.

The display unit 660 may display information on a state of the air conditioner 1000. For example, the display unit 660 may display information on pollution levels of the photocatalyst filter 100, information on a replacement timing of the photocatalyst filter 100, information on packing factors of the photocatalyst beads in the photocatalyst filter 100 (for example, information on the number of filled photocatalyst beads, packing factors at each point in time, whether or not the photocatalyst beads need to be filled, or the like), information on a state of the photocatalyst filter 100 (for example, information on the number of days used or a cumulative time after the photocatalyst beads are filled), and information on activity that is currently in progress (for example, information on whether or not an air quality sensing process is being performed or a filtering process is being performed or information on a moving direction of air). The information as described above may be provided for each of the plurality of internal spaces of the photocatalyst filter 100. Meanwhile, the information as described above may be provided through the display unit 660. Alternatively, according to another exemplary embodiment, the information as described above may be provided to a user from an external apparatus such as a smart phone communicating with the air conditioner 1000. According to an exemplary embodiment, user interfaces (UIs) including the information as described above may be displayed on the display unit 660 or on an external apparatus such as a smart phone communicating with the air conditioner 1000.

Various examples of the UIs that may be displayed on the display unit 660 or the external apparatus such as the smart phone communicating with the air conditioner 1000 will hereinafter be described.

FIG. 16 is views for describing UIs indicating pollution levels of photocatalyst beads. The UIs of FIG. 16 represent shapes of the photocatalyst beads filled in the photocatalyst filter 100. According to an exemplary embodiment of the present disclosure, the photocatalyst beads may be formed of a material which changes color depending on pollution levels. An example of a chemical material which changes color depending on gas adsorption may include chlorophenol red, bromocresol green, bromophenol blue, bromothymol blue, cresol red, methyl orange, methyl red, phenol red, phenolphthalein, thymol blue, m-cresol purple, an enaminone based compound, a β-diketone/amine pair based compound, and the like.

Figure 16A:
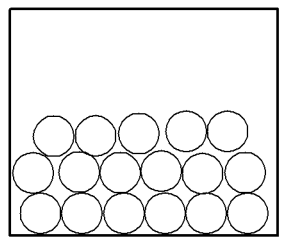
Figure 16B:
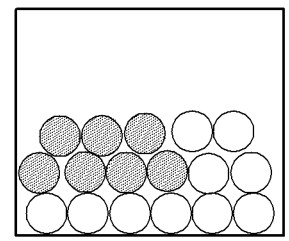
Figure 16C:
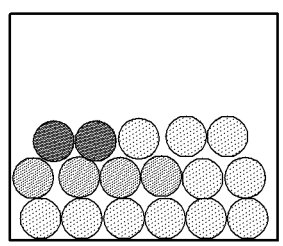
Figure 16D:
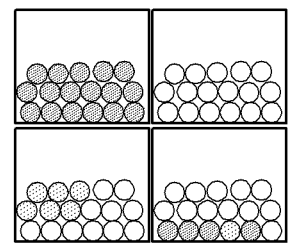

Referring to FIGS. 16(a), 16(b), and 16(c), photocatalyst beads having colors which change depending on pollution levels may be displayed on the UIs. For example, the deeper the color of the photocatalyst beads, the higher the pollution levels. In addition, information on the pollution levels for each of the internal spaces of the photocatalyst filter 100 may be provided to an UI as illustrated in (d) of FIG. 16.

FIGS. 17(a), 17(b), 17(c), and 17(d) are views for describing a method of providing information on pollution levels of the photocatalyst filter 100 in various manners. UIs may provide information for each of the internal spaces of the photocatalyst filter 100. FIG. 17 illustrates a case in which the photocatalyst filter 100 includes four internal spaces.

Figure 17A:
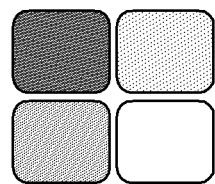
Figure 17B:
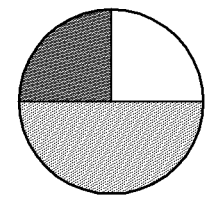
Figure 17C:
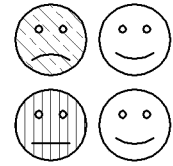
Figure 17D:
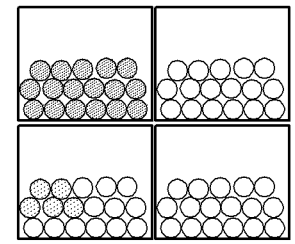

Referring to FIGS. 17(a), 17(b), 17(c), and 17(d), UIs in which pollution levels of the respective internal spaces of the photocatalyst filter 100 are represented by colors may be provided. For example, the higher the pollution levels, the deeper the colors. FIG. 17(c) represents pollution levels through facial expressions. In addition, FIG. 17(d) represents pollution levels by colors of the photocatalyst beads in the photocatalyst filter. For example, the deeper the colors of the photocatalyst beads, the higher the pollution levels.

Meanwhile, FIG. 17(d) may be an image obtained by actually capturing an image of the photocatalyst filter 100. For example, the photocatalyst beads may be formed of a chemical material which changes color when a harmful gas is adsorbed on a surface thereof, and a camera for capturing an image of the photocatalyst filter 100 may be disposed in the air conditioner 1000. The captured image is transmitted to a user terminal, or the like, communicating with the air conditioner 1000, such that the UI as illustrated in FIG. 17(d) may be provided on the user terminal.

FIG. 18 is a view for describing a filter replacement period informing manner according to an exemplary embodiment of the present disclosure.

When a harmful gas is introduced into the air conditioner 1000, at least one of photocatalyst filter 1 or photocatalyst filter 2 may be operated depending on a result sensed by a sensor for sensing an air quality, disposed in the air conditioner 1000. Photocatalyst filter 1 or photocatalyst filter 2 may be photocatalyst filters in which different kinds of photocatalyst beads are filled to filter different kinds of gases. For example, when the introduced gas is a gas that needs to be filtered through photocatalyst filter 1 as a sensing result, only photocatalyst filter 1 may be operated. An example of allowing only photocatalyst filter 1 to be operated may include a method of allowing air to be introduced into only photocatalyst filter 1 by controlling an introduction path of the air, a method of irradiating light to only photocatalyst filter 1, or the like.

As described above, the photocatalyst beads filled in the photocatalyst filter may be formed of the chemical material which changes color when the gas is adsorbed, and colors of the photocatalyst beads may change depending on an adsorption concentration. For example, the higher the adsorption concentration, the deeper the colors. An apparatus such as a camera, or the like, may be disposed in the air conditioner 1000 to capture an image of the photocatalyst filter, and the captured image may be analyzed to decide pollution levels of the photocatalyst beads on the basis of the colors of the photocatalyst beads and inform a user of a filter replacement period depending on the pollution levels. In this case, the captured image may be provided to an external apparatus such as a smart phone. Alternatively, an external housing of the air conditioner 1000 may be formed of a transparent or translucent material, such that the user may directly observe changes in the colors of the photocatalyst beads in the photocatalyst filter with his/her eyes.

According to an exemplary embodiment in the present disclosure, a light source unit 210 may reconfigure the photocatalyst beads by irradiating ultraviolet (UV) to a polluted photocatalyst filter in a state in which the air conditioner 1000 is not operated. Therefore, as illustrated in FIG. 18, the photocatalyst beads of photocatalyst filter 1 that are polluted may be reconfigured.

FIG. 19 is a view for describing a gas analyzing manner according to an exemplary embodiment of the present disclosure.

Referring to FIG. 19, it may be analyzed which gas is introduced and decomposed in a large amount through changes in colors of the photocatalyst beads filled in the photocatalyst filter. For example, surfaces of the photocatalyst beads may be coated with a chemical material which changes color to red when it reacts to formaldehyde, changes color to green when it reacts to ammonia, and changes color to blue when it reacts to acetaldehyde. Alternatively, several photocatalyst beads may be configured so that they change color when they react to formaldehyde, and the other photocatalyst beads may be configured so that they change color when they react to ammonia. The chemical material coated on the surfaces of the photocatalyst beads may be a material that reacts differently to harmful gases depending on the kind of harmful gases. An external housing of the air conditioner 1000 may be formed of a transparent or translucent material, such that the user may directly view changes in the colors of the photocatalyst beads in the photocatalyst filter with his/her eyes to analyze the introduced gas, or an image analysis may be performed on an image of the photocatalyst beads captured through a camera, or the like, provided in the air conditioner 1000 to analyze the introduced gas. An air quality deterioration factor in the home for a predetermined period may be determined through an analysis result.

FIGS. 20(a), 20(b), 20(c), and 20(d) are views for describing various UIs providing information on packing factors of photocatalyst beads in the photocatalyst filter 100. The UIs may be displayed on the display unit 660 or on an external apparatus such as a smart phone.

Figure 20A:
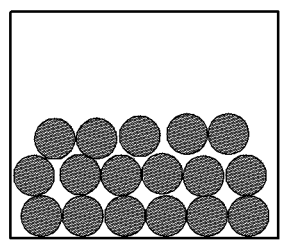
Figure 20B:
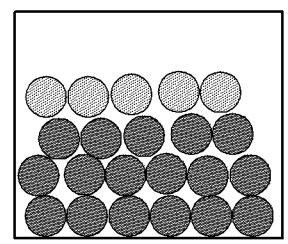

Referring to FIGS. 20(a), 20(b), 20(c), and 20(d), the UIs informing the user of an amount of the photocatalyst beads filled in the photocatalyst filter 100 may be provided. When FIG. 20(a) illustrates an amount of photocatalyst beads in the beginning, FIG. 20(b) illustrates an amount of photocatalyst beads that are added. The added photocatalyst beads may have a different color from that of the previously existing photocatalyst beads, may have a size that is smaller than that of the previously existing photocatalyst beads, or may have a size that is different than that of the previously existing photocatalyst beads, depending on pollution levels. The photocatalyst beads are manufactured in several colors to allow the user to readily select and fill appropriate photocatalyst beads. For example, orange photocatalyst beads may be for removing formaldehyde, and green photocatalyst beads may be for removing acetaldehyde. A manual including information on the colors of the photocatalyst beads may be provided together with the photocatalyst beads at the time of purchasing the photocatalyst beads. Such a manual may be provided in an electronic data form. The user may download and use the manual using an apparatus such as a smart phone. For example, the manual may include information on heights to which the photocatalyst beads should be filled in the respective internal spaces of the photocatalyst filter 100, as illustrated in FIG. 21(a), or may include a guide such as "put orange beads by two spoons", as illustrated in FIG. 21(b).

Figure 20C:
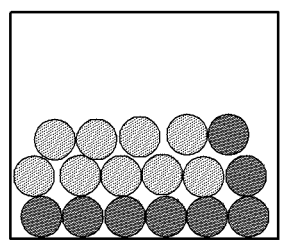
Figure 20D:
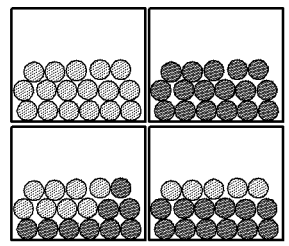
Figure 21A:
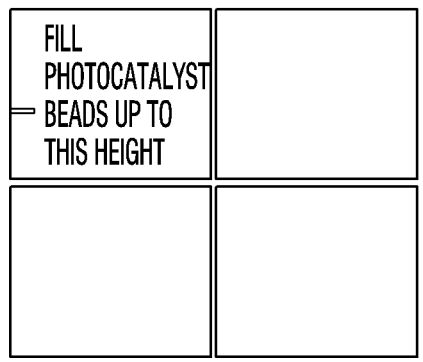
Figure 21B:
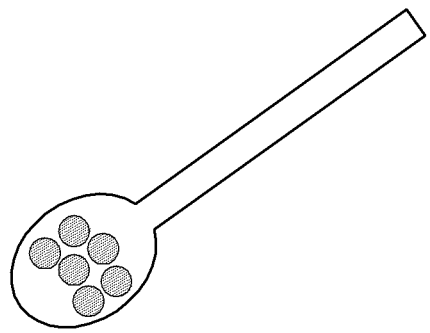
Figure 24A:
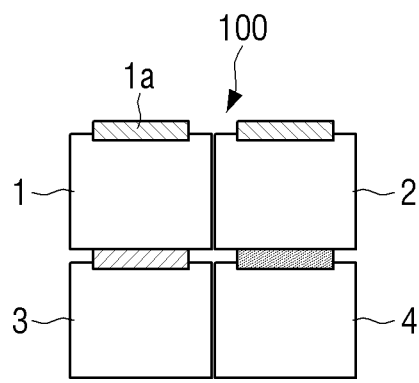
Figure 24B:
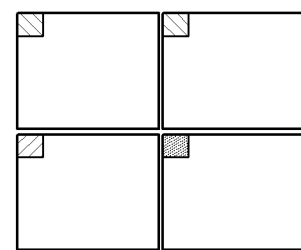
Figure 24C:
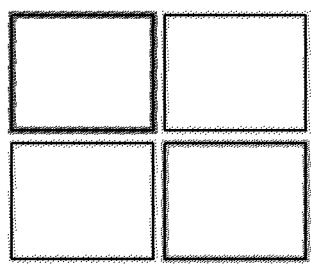
Figure 24D:
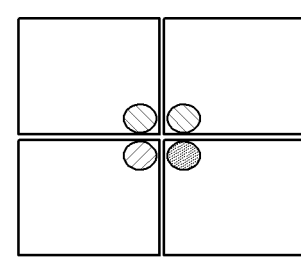

FIG. 20(c) illustrates that some of the existing photocatalyst beads have been replaced by new photocatalyst beads. In addition, information on the packing factors for each of the internal spaces of the photocatalyst filter 100 may be provided to an UI as illustrated in FIG. 20(d). According to an exemplary embodiment of the present disclosure, colors of the respective photocatalyst beads in each filling timing may be configured to be different from one another to allow old photocatalyst beads to be distinguishable by their color. Therefore, the user may more easily replace the old photocatalyst beads with new photocatalyst beads.

FIGS. 22(a), 22(b), 22(c), 22(d), and 22(e) are views for describing a method of providing information on packing factors in the respective internal spaces of the photocatalyst filter 100 in various manners.

Referring to FIGS. 22(a) and 22(b), UIs in which packing factors of the respective internal spaces of the photocatalyst filter 100 are represented by colors may be provided. Referring to FIG. 22(a), it may be appreciated which kinds of photocatalyst beads and how much photocatalyst beads are disposed in the respective internal spaces of the photocatalyst filter 100. For example, photocatalyst beads for removing a first gas may be represented by a deep color, and photocatalyst beads for removing a second gas may be represented by a light color. The packing factors of the photocatalyst beads may be represented by % as illustrated in FIG. 22(b), may be represented by sizes of colors filled in figures as illustrated in FIG. 22(c), may be represented by different colors as illustrated in FIG. 22(d), and may be represented by the numbers of photocatalyst beads as illustrated in FIG. 22(e).

FIGS. 23(a), 23(b), 23(c), 23(d), and 23(e) are views for describing various UIs providing information on an operation state of the photocatalyst filter 100.

Activity regions in the respective internal spaces of the photocatalyst filter 100 may be represented by colors through a UI as illustrated in FIG. 23(a). Referring to FIG. 23(b), information on the numbers of days the photocatalyst beads have been used in the respective internal spaces of the photocatalyst filter 100 may be provided. Referring to FIG. 23(c), information on a moving direction of air into the photocatalyst filter 100 may be provided in, for example, an arrow shape. Referring to FIG. 23(d), information on an operation progress situation of the photocatalyst filter or an operation progress situation of the sensor may be provided. Referring to FIG. 23(e), information identifying the internal space or spaces within which filtering is performed, a flow velocity of the air, and the like, may be represented through an animation in which the photocatalyst beads are blown off by passage of air in the respective internal spaces of the photocatalyst filter 100. FIGS. 24(a), 24(b), 24(c), and 24(d) are views for describing the use of light emitting diodes (LEDs) disposed in the photocatalyst filter according to an exemplary embodiment of the present disclosure.

FIG. 24 illustrates the photocatalyst filter 100 including four internal spaces, and LEDs may be disposed in the respective internal spaces of the photocatalyst filter 100. The LEDs may be disposed on one surface of each of the respective internal spaces as illustrated in FIG. 24(a), may be disposed on one corner of each of the respective internal spaces as illustrated in FIGS. 24(b) and 24(d), or may be disposed to surround the walls of each of the photocatalyst filters 100 as illustrated in FIG. 24(c). The LEDs disposed in the photocatalyst filter 100 as described above may be turned on to provide information for each internal space. For example, information on pollution levels, reproduction rates, and packing factors of the photocatalyst beads, kinds of harmful gases, and the like, for each internal space may be represented by the number of times the LEDs are turned on, the colors of the LEDs, times at which the LEDs are turned on, and the like. For example, in a case in which replacement of the photocatalyst beads filled in the first internal space 1 of the photocatalyst filter 100 is required, an LED 1a disposed in the first internal space 1 may be controlled to be flickered. In a case in which the air conditioner 1000 is transparent or translucent, the user may observe the on or off state of the LEDs to determine a state of the photocatalyst filter 100.

Accordingly to another exemplary embodiment of the present disclosure, the LEDs are not disposed in the photocatalyst filter, and the information on the state of the photocatalyst filter may also be provided to the user through a user terminal such as a smart phone. Referring to FIG. 25, the photocatalyst filter 100 does not include the LEDs, unlike FIG. 24, and the information on the photocatalyst filter may be displayed on an external apparatus 200 communicating with the air conditioner 1000. The external apparatus 200 may communicate with the air conditioner 1000 in a communication manner such as Bluetooth, or the like.

Figure 7:
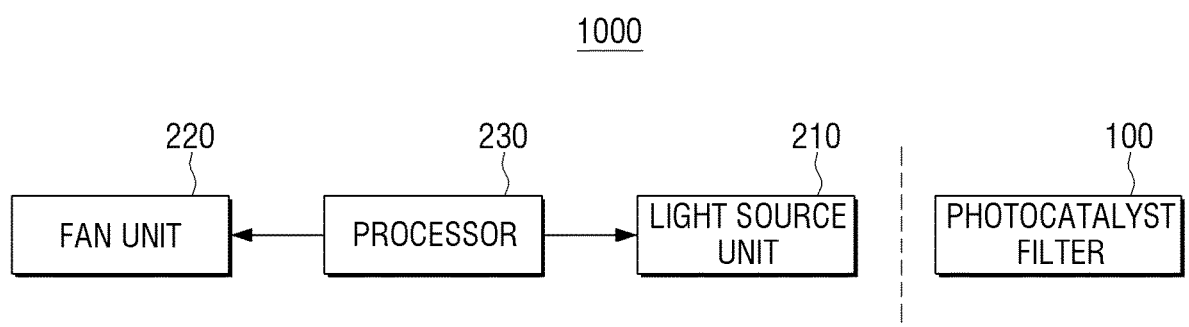
FIG. 7 is a block diagram for describing components of the air conditioner according to an exemplary embodiment of the present disclosure.

FIG. 7 is a block diagram for describing components included in the air conditioner 1000 described with reference to FIG. 6.

Referring to FIG. 7, the air conditioner 1000 includes the photocatalyst filter 100, the light source unit 210, a fan unit 220, and a processor 230.

A repetitive description of the photocatalyst filter 100 will be omitted.

The light source unit 210 is a component for irradiating light onto the photocatalyst filter 100. A photocatalyst material of the photocatalyst filter 100 may react to the light irradiated from the light source unit 210 to remove harmful gases, odor materials, microorganisms, and the like.

The light source unit 210 may emit light appropriate for generating a photocatalyst reaction in the photocatalyst material included in the photocatalyst filter 100. For example, the light source unit 210 may be implemented by elements such as fluorescent lamps or incandescent lamps or LEDs, and may emit light having a wavelength range such as white light, red light, green light, blue light, ultraviolet light (about 10 to 400 nm), visible light (about 400 to 700 nm), infrared light (about 700 nm to 1 mm), near infrared (NIR) light (about 0.75 to 1.4 μm), short-wave infrared (SWIR) light (about 1.4 to 3 μm), medium-wave infrared (MWIR) light (about 3 to 8 μm), long-wave infrared (LWIR) light (8 to 15 μm), far infrared (FIR) light (about 15 to 1000 μm), and the like.

For example, the light source unit 210 may include an optical concentrator (for example, a Fresnel lens, a convex lens, a concave lens, or the like), and include a color filer, and thereby, the brightness, the illumination color, the color temperature, the light focusing (region), and the like, of the light source unit 210 may be controlled by the processor 230.

The fan unit 220 is a component for allowing air within a space external to the air conditioner to be introduced into the body 610 through the inlet 611. The air introduced through the inlet 611 passes through the photocatalyst filter 100, such that impurities in the air are filtered through the photocatalyst filter 100.

The processor 230 is a component that may control the general operation of the air conditioner 1000, and may include, for example, at least one central processing unit (CPU) (or digital signal processor (DSP), micro processor unit (MPU), or the like), a random access memory (RAM), a read only memory (ROM), and a system bus. The processor 230 may be implemented by a micro computer (MICOM), an application specific integrated circuit (ASIC), or the like.

The processor 230 may control the driving of the fan unit 220 and the light source unit 210. In addition, the processor 230 may provide the various UIs as described above through the display unit 660 or may provide the various UIs as described above to an external apparatus through communication with another apparatus. The air conditioner 1000 may include a communication unit for the purpose of communication with another apparatus. The communication unit may be connected to the external apparatus through, for example, a local area network (LAN) and an Internet network, or may be connected to the external apparatus in a wireless communication manner (for example, Z-wave, 4Lo wireless personal area network (WPAN), radio-frequency identification (RFID), long-term evolution (LTE) device to device (D2D), Bluetooth low energy (BLE), general packet radio service (GPRS), Weightless, ZigBee, Edge ZigBee, ANT+, near field communication (NFC), infrared data association (IrDA), digital enhanced cordless telecommunications (DECT), wireless local area network (WLAN), Bluetooth, WiFi, WiFi direct, global system for mobile (GSM), universal mobile telecommunications system (UMTS), LTE, wireless broadband (WiBRO), Cellular (3/4/5G), ultrasonic wave, or the like).

The air conditioner 1000 may provide various information to another apparatus through the communication unit. For example, the processor 230 may transmit state information (for example, information for informing the user of a filter replacement timing) of the air conditioner 1000 to a user terminal apparatus (for example, a smart phone, a tablet personal computer (PC), a smart watch, or the like), or may transmit a control command for controlling another apparatus (for example, controlling a window opening or closing apparatus to open a window or controlling a robot cleaner to perform cleaning) on the basis of a result sensed by a sensor disposed in the air conditioner 1000 and sensing an air quality.

In addition, a camera for capturing an image of the photocatalyst filer 100 may be disposed in the air conditioner 1000, and the processor 230 may analyze the photocatalyst beads filled in the photocatalyst filter 100 from an image obtained by capturing the photocatalyst beads, and may provide information on pollution levels of the photocatalyst beads, the type or types of introduced gases, packing factors of the photocatalyst beads, a replacement timing of the photocatalyst beads, whether or not the photocatalyst beads need to be reconfigured, a reconfiguration state of the photocatalyst beads, and the like, through the display unit 660 or transmit the information as described above to the external apparatus such as the smart phone, or the like, in a communication manner such as Bluetooth, or the like.

Figure 8:
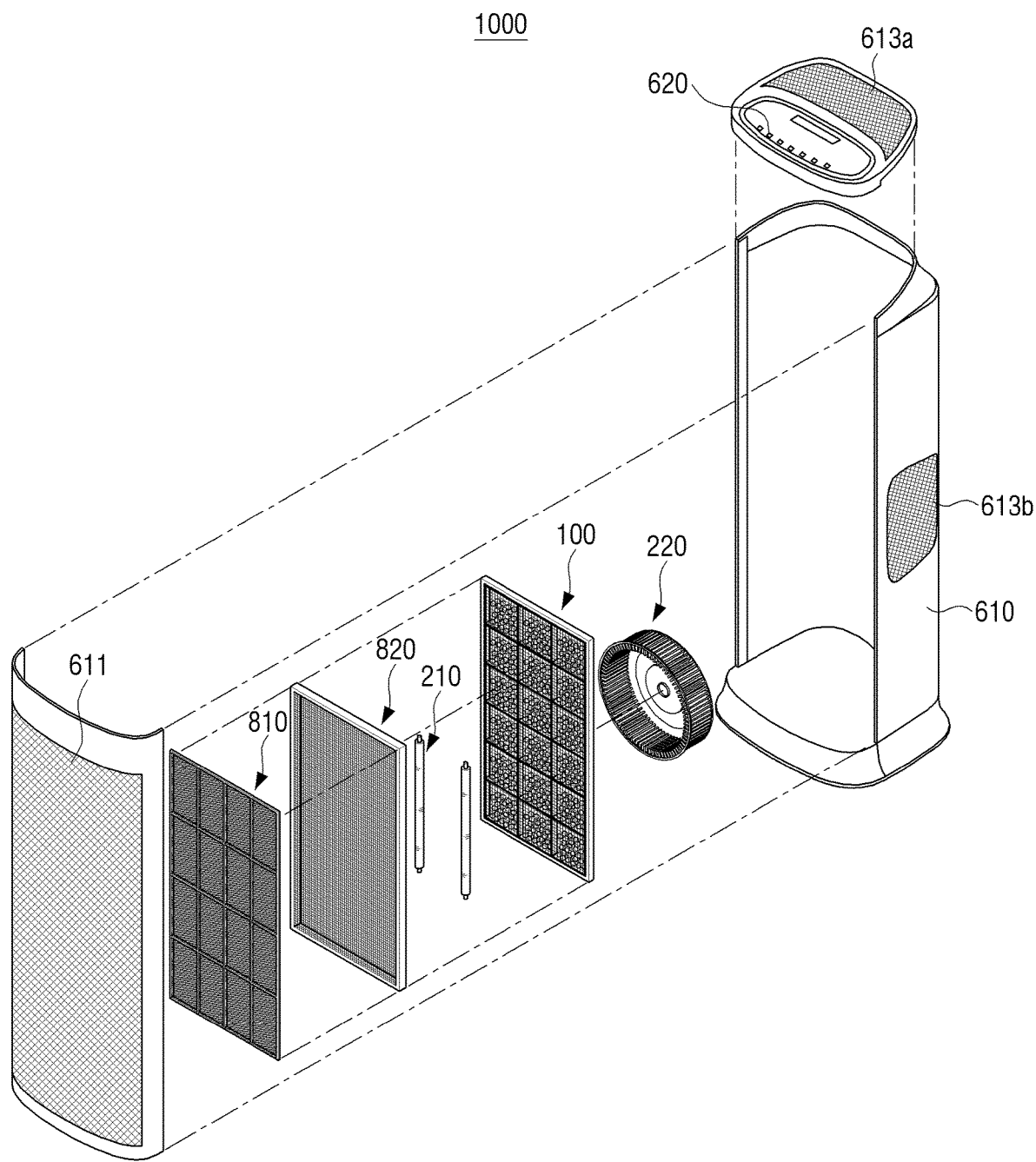
FIG. 8 is an exploded perspective view illustrating the air conditioner according to an exemplary embodiment of the present disclosure.

FIG. 8 is a schematic exploded perspective view illustrating the air conditioner 1000 according to an exemplary embodiment of the present disclosure.

Referring to FIG. 8, the air conditioner 1000 includes the light source unit 210, the photocatalyst filter 100, and the fan unit 220 as described above with reference to FIG. 7 disposed in the body 610. The air conditioner 1000 may further include a free filter 810 and a high efficiency particulate air (HEPA) filter 820. In addition, the air conditioner 1000 may further include a deodorizing filter (not illustrated) disposed between the free filter 810 and the HEPA filter 820 and including activated carbon. The filters may be disposed in a sequence as illustrated in FIG. 8 or be disposed in another sequence. Meanwhile, although a case in which one photocatalyst filter 100 exists in the air conditioner 1000 is illustrated in FIG. 8, the air conditioner may include a plurality of photocatalyst filters.

Relatively large dust particles are primarily filtered by the free filter 810. The HEPA filter 820 is a component for filtering fine dust, or the like, that is not filtered in the free filter 810, and may be formed of, for example, glass fibers.

The light source unit 210 irradiates ultraviolet light or visible light onto the photocatalyst filter 100. Although a case in which the light source unit 210 is disposed on one surface of the photocatalyst filter 100 is illustrated in FIG. 8, the light source unit 210 is not necessarily limited to being disposed in such a form, but may also be provided on each of opposite surfaces of the photocatalyst filter 100, respectively. In addition, the light source unit 210 is not necessarily disposed to face the photocatalyst filter 100, but may be disposed at any position appropriate for irradiating light onto the photocatalyst filter 100.

Figure 9:
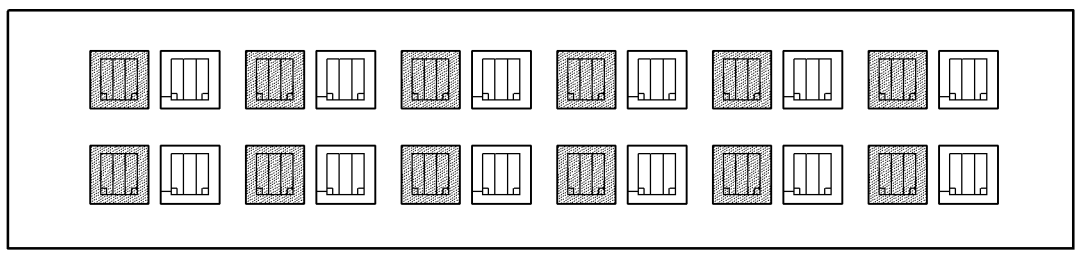
FIGS. 9 and 10 are views for describing a light source portion of an air conditioner according to diverse exemplary embodiments of the present disclosure.

Although a case in which the light source unit 210 is a lamp is illustrated in FIG. 8, the light source unit 210 may also be implemented by a chip in which a plurality of light emitting elements are disposed on a substrate as illustrated in FIG. 9, according to another exemplary embodiment.

Figure 10:
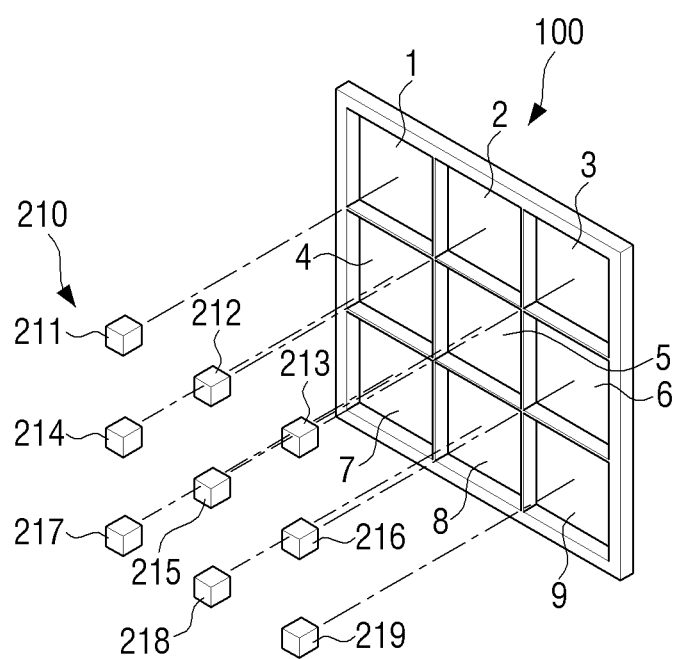

The light source unit 210 may include a plurality of light emitting elements, and the number of light emitting elements may be determined depending on an amount of light required by the photocatalyst filter 100. For example, the light source unit 210 may have light emitting elements in a number corresponding to the number of internal spaces configuring the photocatalyst filter 100. In this case, for example, as illustrated in FIG. 10, the plurality of light emitting elements 211 to 219 included in the light source unit 210 may be disposed at positions corresponding to the positions of the plurality of internal spaces 1 to 9 included in the photocatalyst filter 100. The plurality of light emitting elements 211 to 219 may be attached to, for example, the covers 110a and 110b of the photocatalyst filter 100. Alternatively, the plurality of light emitting elements may be disposed on a separate substrate, and the separate substrate may be disposed to face the photocatalyst filter 100. However, the number of light emitting elements of the light source unit 210 does not need to coincide with the number of internal spaces configuring the photocatalyst filter 100 as illustrated in FIG. 10, but may be different from the number of internal spaces. For example, the light source unit 210 may include only one light emitting element, and one light emitting element may be disposed to irradiate light onto the photocatalyst filter 100. Even in the case in which the light source unit 210 includes only one light emitting element, the light may be uniformly provided to each of the respective internal spaces of the photocatalyst filter 100 using, for example, the light reflecting structures 51 to 54 as described above with reference to FIG. 5.

Meanwhile, according to an exemplary embodiment, the light source unit 210 may be moved and rotated within the air conditioner 1000, and may appropriately provide the light at required places while being moved and rotated.

According to an exemplary embodiment of the present disclosure, the air conditioner 1000 may further include a sensor (not illustrated) for measuring an air quality. The sensor may be disposed adjacent to the inlet 611 through which the air is introduced.

The sensor may measure a kind, a concentration, and the like, of material included in the air. For example, the sensor may be a gas sensor. As the gas sensor, a semiconductor type gas sensor, a catalytic combustion method gas sensor, an electrochemical gas sensor, an optical gas sensor, a color conversion gas sensor, or the like, may be used depending on a measurement principle. An semiconductor type gas sensor senses a gas by a change in a resistance of a metal oxide depending on a reaction to the gas. An electrochemical gas sensor senses a gas by a change in electromotive force between reaction and reference electrodes by a reaction to the gas. A catalytic combustion method gas sensor senses a gas by a change in a resistance of a hot wire by a heat generation reaction to a combustible gas. An optical gas sensor senses a gas by a change in an infrared absorbance by the gas. A color conversion gas sensor is a sensor including an indication dye which changes color through a reaction to a target material to be measured, and may determine a material through a color change.

In addition, the sensor may include, for example, a dust sensor. The dust sensor is operated in a principle that an infrared ray irradiated from an LED is scattered by dust when dust, introduced from the outside, passes through a measurement region, and the scattered infrared ray is sensed by an infrared detector. In addition, the air conditioner 1000 may further include a temperature sensor, a humidity sensor, and the like, as well as the sensor for sensing the air quality described above.

The processor 230 may determine the air quality on the basis of a result sensed by the sensor, and may control a moving path of the air depending on the determined air quality, and control the fan unit 220 and the light source unit 210.

Figure 11:
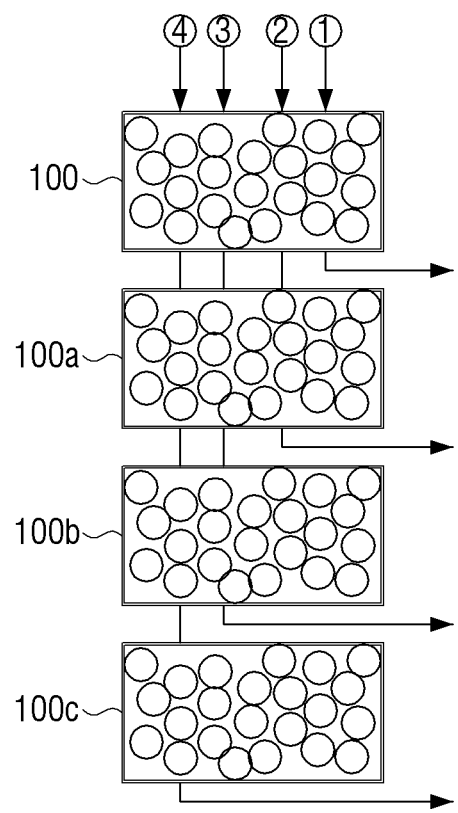
FIGS. 11 to 14 are views for describing a photocatalyst filter of an air conditioner according to diverse exemplary embodiments of the present disclosure.

The processor 230 may determine that the air quality is any one of, for example, four steps (very good, good, bad, and very bad) on the basis of the result sensed by the sensor. In addition, the processor 230 may control the moving path of the air depending on the determined air quality. An exemplary embodiment for a control of the moving path of the air will hereinafter be described with reference to FIG. 11. FIG. 11 illustrates an exemplary embodiment in which additional photocatalyst filters 100a, 100b, and 100c as well as the photocatalyst filter 100 described above are included in the air conditioner 1000. Hereinafter, for convenience of explanation, reference number 100 denotes a first photocatalyst filter, reference numeral 100a denotes a second photocatalyst filter, reference numeral 100b denotes a third photocatalyst filter, and reference numeral 100c denotes a fourth photocatalyst filter.

When it is decided that air ①  of which an air quality is determined to be very good on the basis of the result sensed by the sensor is introduced, the processor 230 may control a channel of the air so that the air passes through only the first photocatalyst filter 100; when it is decided that air ② of which an air quality is determined to be good on the basis of the result sensed by the sensor is introduced, the processor 230 may control a channel of the air so that the air passes through the first photocatalyst filter 100 and the second photocatalyst filter 100a; when it is decided that air ③ of which an air quality is determined to be bad on the basis of the result sensed by the sensor is introduced, the processor 230 may control a channel of the air so that the air passes through the first photocatalyst filter 100, the second photocatalyst filter 100a, and the third photocatalyst filter 100b; and when it is decided that air ④ of which an air quality is determined to be very bad on the basis of the result sensed by the sensor is introduced, the processor 230 may control a channel of the air so that the air passes through the first photocatalyst filter 100, the second photocatalyst filter 100a, the third photocatalyst filter 100b, and the fourth photocatalyst filter 100c.

According to the manner as described above, air of which an air quality is bad passes through a large number of photocatalyst filters, such that a removal rate of harmful materials may be increased. In addition, air of which an air quality is not bad passes through only some of the photocatalyst filters, such that a filtering speed may be increased. In this case, the others of the photocatalyst filters are not used, such that lifespans of the others of the photocatalyst filters may be increased.

Although the channels of the air are simply illustrated by arrows in FIG. 11, when describing an example of a method of controlling the channels of the air in detail, air channel blocking apparatuses (not illustrated) may be disposed between adjacent ones of the plurality of photocatalyst filters 100, 100a, 100b, and 100c and the processor 230 may control the air channel blocking apparatuses to be opened or closed. For example, when it is decided that the air of ① which the air quality is determined to be very good is introduced, the processor 230 may close an air channel blocking apparatus disposed between the first photocatalyst filter 100 and the second photocatalyst filter 100a to prevent the air from being moved to the second photocatalyst filter 100a, and when it is decided that the air ② of which the air quality is determined to be good is introduced, the processor 230 may open the air channel blocking apparatus disposed between the first photocatalyst filter 100 and the second photocatalyst filter 100a and close an air channel blocking apparatus disposed between the second photocatalyst filter 100a and the third photocatalyst filter 100b to prevent the air from being moved to the third photocatalyst filter 100b.

Although the processor 230 may control a flow of the air by physical components such as the channel blocking apparatuses as described above, the processor 230 may also control a flow of the air by controlling driving of the fan unit 220, according to another exemplary embodiment.

Although a case in which each of the plurality of photocatalyst filters includes the same kind of photocatalyst beads 10 is illustrated in FIG. 11, each of the plurality of photocatalyst filters may include different kinds of photocatalyst beads, according to another exemplary embodiment of the present disclosure. This will be described with reference to FIGS. 12A to 12C.

Figure 12A:
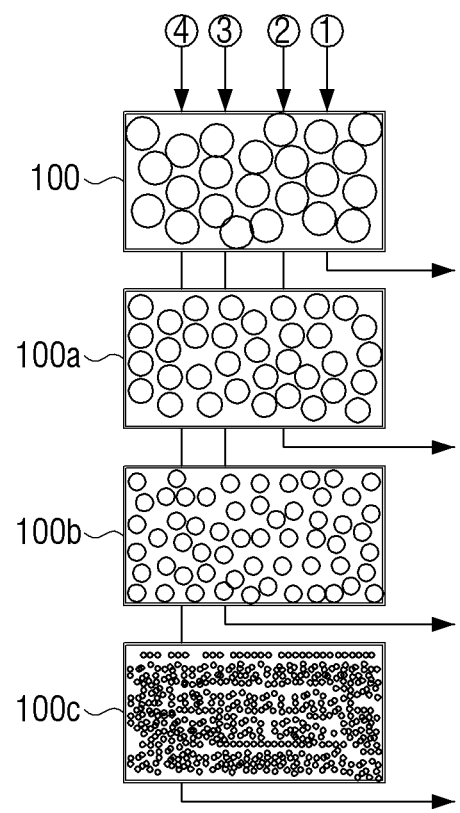

In an exemplary embodiment described with reference to FIG. 12A, channels of air may be controlled depending on an air quality, as described above with reference to FIG. 11. However, unlike the description with reference to FIG. 11, sizes of photocatalyst beads 10 included in the plurality of photocatalyst filters 100, 100a, 100b, and 100c become gradually smaller. As the sizes of the photocatalyst beads 10 become smaller, contact areas between the photocatalyst beads and the air are increased, such that filtering performance is increased. According to the exemplary embodiment described with reference to FIG. 12A, as the air quality becomes worse, the number of photocatalyst filters through which the air should pass is increased, and the air should pass through smaller photocatalyst beads, such that the air of which the air quality is bad may be more effectively purified.

Figure 12B:
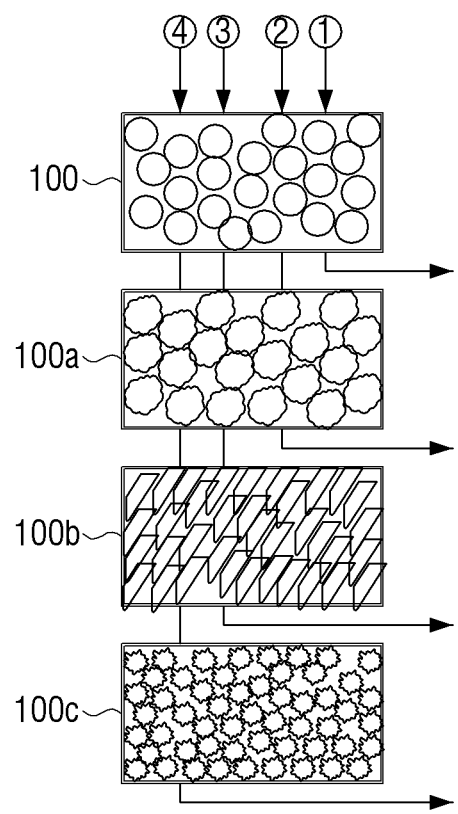

In an exemplary embodiment described with reference to FIG. 12B, channels of air may be controlled depending on an air quality, as described above with reference to FIG. 11. However, unlike the description with reference to FIG. 11, forms of photocatalyst beads 10 included in the plurality of photocatalyst filters 100, 100a, 100b, and 100c are different from one another. Contact areas between the photocatalyst beads and the air become larger in a sequence of the first photocatalyst filter 100, the second photocatalyst filter 100a, the third photocatalyst filter 100b, and the fourth photocatalyst filter 100c.

Figure 12C:
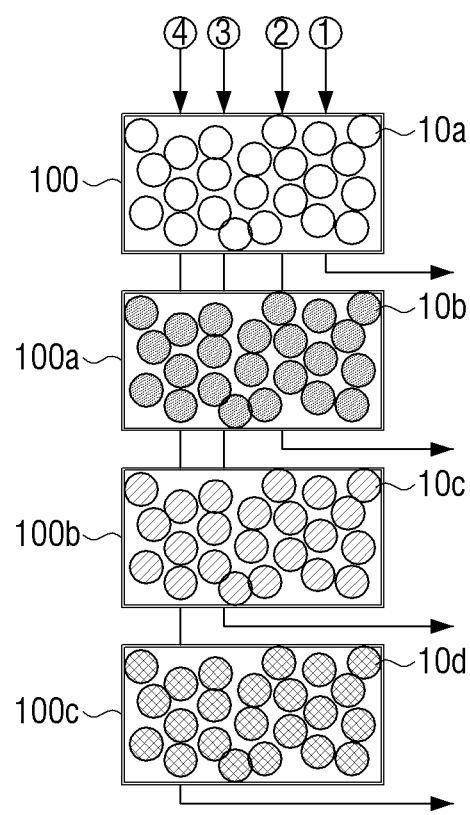

In the exemplary embodiment described with reference to FIG. 12C, channels of air may be controlled depending on an air quality, as described above with reference to FIG. 11. However, unlike the description with reference to FIG. 11, materials configuring the photocatalyst beads included in the plurality of photocatalyst filters 100, 100a, 100b, and 100c are different from one another. For example, photocatalyst beads 10a included in the first photocatalyst filter 100, photocatalyst beads 10b included in the second photocatalyst filter 100a, photocatalyst beads 10c included in the third photocatalyst filter 100b, and photocatalyst beads 10d included in the fourth photocatalyst filter 100c are different in photocatalyst materials from one another or are different in materials (for example, adsorbents) additionally included in the photocatalyst materials from one another.

According to another exemplary embodiment of the present disclosure, the same effects as those of the exemplary embodiments described above with reference to FIGS. 11 to 12C may be obtained by a method of activating or inactivating each of the plurality of photocatalyst filters instead of the manner of controlling the flow of the air as described above. A phrase "activating the photocatalyst filter" means that light is irradiated onto the photocatalyst filter to out the photocatalyst filter into a state in which a photocatalytic reaction may occur, while a phrase "deactivating the photocatalyst filter" means that light is not irradiated onto the photocatalyst filter, such that no photocatalytic reaction will occur. The present exemplary embodiment will hereinafter be described with reference to FIGS. 13A to 13D.

Figure 13A:
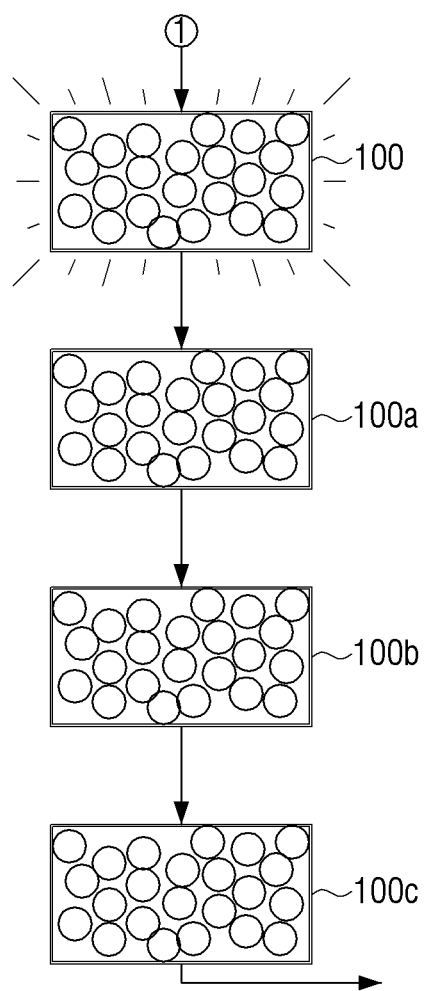
Figure 13B:
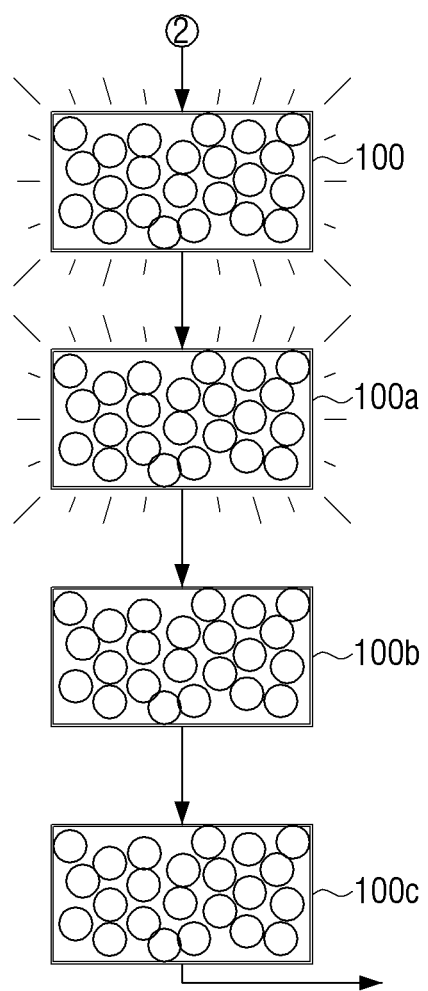
Figure 13C:
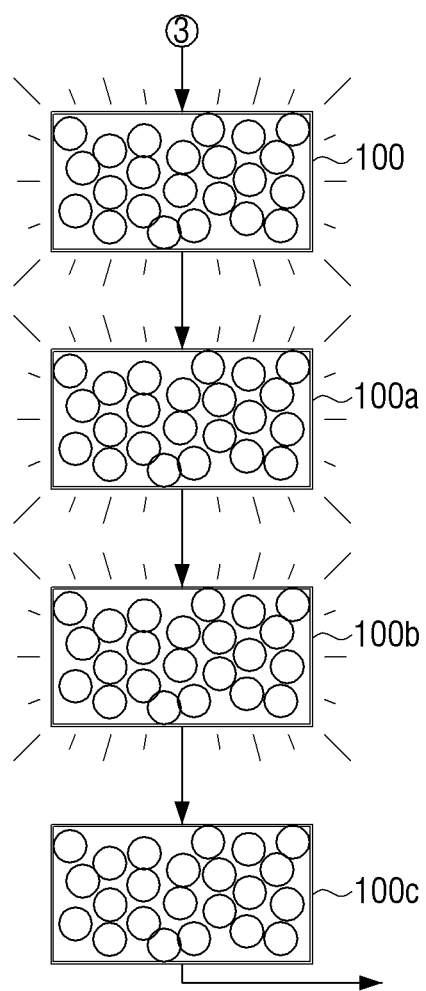
Figure 13D:
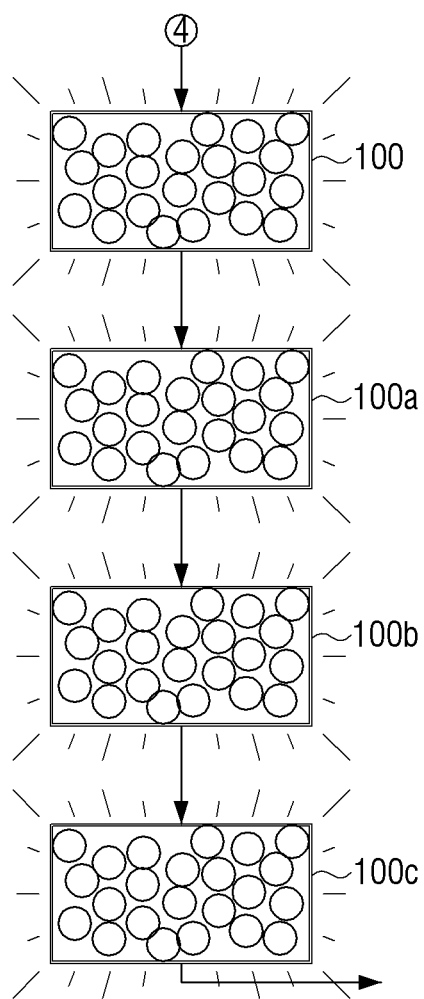

In detail, when it is decided that air ① of which an air quality is determined to be very good is introduced, the processor 230 may control the light source unit 210 to irradiate light onto the first photocatalyst filter 100 as illustrated in FIG. 13A; when it is decided that air ② of which an air quality is determined to be good is introduced, the processor 230 may control the light source unit 210 to irradiate light onto the first photocatalyst filter 100 and onto the second photocatalyst filter 100a as illustrated in FIG. 13B; when it is decided that air of which an air quality is determined to be bad is introduced, the processor 230 may control the light source unit 210 to irradiate light onto the first photocatalyst filter 100, onto the second photocatalyst filter 100a, and onto the third photocatalyst filter 100b as illustrated in FIG. 13C; and when it is decided that air ④ of which an air quality is determined to be very bad is introduced, the processor 230 may control the light source unit 210 to irradiate light onto the first photocatalyst filter 100, onto the second photocatalyst filter 100a, onto the third photocatalyst filter 100b, and onto the fourth photocatalyst filter 100c as illustrated in FIG. 13D.

In this case, according to an exemplary embodiment, the light source unit 210 may include a first light source dedicated to the first photocatalyst filter 100, a second light source dedicated to the second photocatalyst filter 100a, a third light source dedicated to the third photocatalyst filter 100b, and a fourth light source dedicated to the fourth photocatalyst filter 100c, and the processor 230 may individually turn on or turn off the first to fourth light sources to individually activate or inactivate the first to fourth photocatalyst filters 100, 100a, 100b, and 100c. According to another exemplary embodiment, instead of providing dedicated light source units to the first to fourth photocatalyst filters 100, 100a, 100b, and 100c, respectively, a direction of light emitted from one light source unit may be controlled by changing angles of, for example, the MEMS mirrors.

According to the exemplary embodiment described above with reference to FIGS. 13A to 13D, there is an advantage that a separate component for controlling the channels of the air is not required. Only some of the photocatalyst filters are activated and photocatalyst reactions do not occur in the others of the photocatalyst filters with respect to the air of which the air quality is not bad, such that lifespans of the others of the photocatalyst filters may be increased, and a larger number of photocatalyst filters are activated with respect to the air of which the air quality is bad, such that a removal rate of harmful materials may be increased.

Also in the exemplary embodiment described above with reference to FIGS. 13A to 13D, various kinds of photocatalyst beads may be used as described above with reference to FIGS. 12A to 12C.

According to another exemplary embodiment of the present disclosure, photocatalyst filters may also be disposed in a manner different from the manners described above with reference to FIGS. 11 to 13D. This will be described with reference to FIG. 14.

Figure 14:
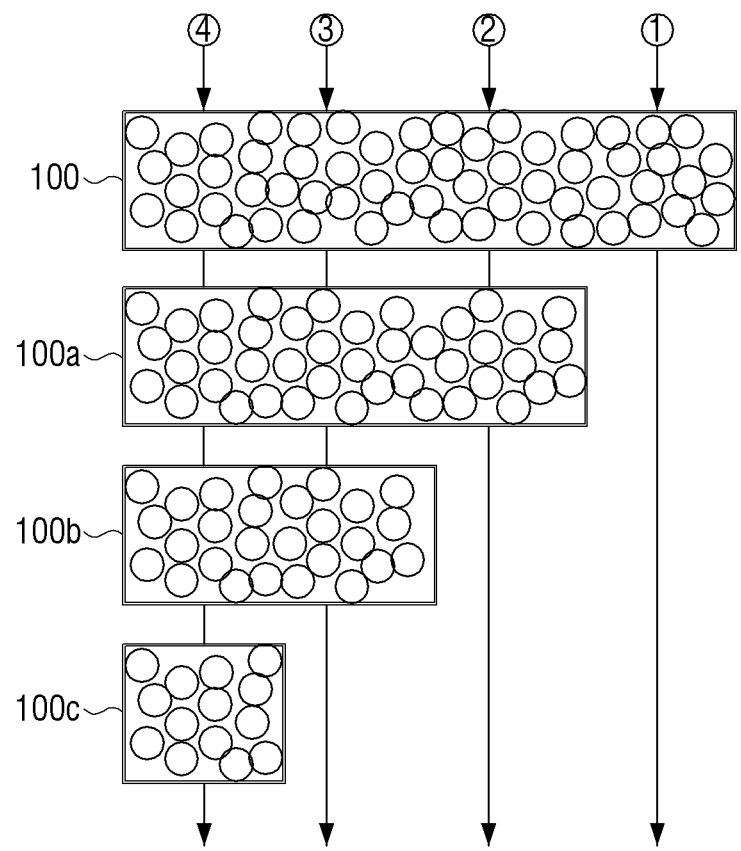

Referring to FIG. 14, when it is decided that air ① of which an air quality is determined to be very good is introduced, the processor 230 may control the fan unit 220 so that the air is introduced in a direction in which it passes through only the first photocatalyst filter 100; when it is decided that air ② of which an air quality is determined to be good is introduced, the processor 230 may control the fan unit 220 so that the air is introduced in a direction in which it passes through the first photocatalyst filter 100 and through the second photocatalyst filter 100a; when it is decided that air ③ of which an air quality is determined to be bad is introduced, the processor 230 may control the fan unit 220 so that the air is introduced in a direction in which it passes through the first photocatalyst filter 100, through the second photocatalyst filter 100a, and through the third photocatalyst filter 100b; and when it is decided that air ④ of which an air quality is determined to be very bad is introduced, the processor 230 may control the fan unit 220 so that the air is introduced in a direction in which it passes through the first photocatalyst filter 100, through the second photocatalyst filter 100a, through the third photocatalyst filter 100b, and through the fourth photocatalyst filter 100c.

Although a case in which the air quality is divided into the four steps is described with reference to FIGS. 11 to 14, this is only an example, and the air quality may be divided into various steps such as two steps, three steps, five steps, and the like. In addition, although a case in which four photocatalyst filters are used is described with reference to FIGS. 11 to 14, this is only an example, and the number of photocatalyst filters that may be used is not limited. Only one single photocatalyst filter may also be used. In the case in which only one single photocatalyst filter is used, the processor 230 may control the light source unit 210 to increase an amount of light as the air quality becomes bad on the basis of the result sensed by the sensor.

According to another exemplary embodiment of the present disclosure, the air conditioner 1000 may include a plurality of photocatalyst filters, and the fan unit 220 may include a plurality of fans each corresponding to one of the plurality of photocatalyst filters. This will be described with reference to FIGS. 15A to 15C.

Figure 15A:
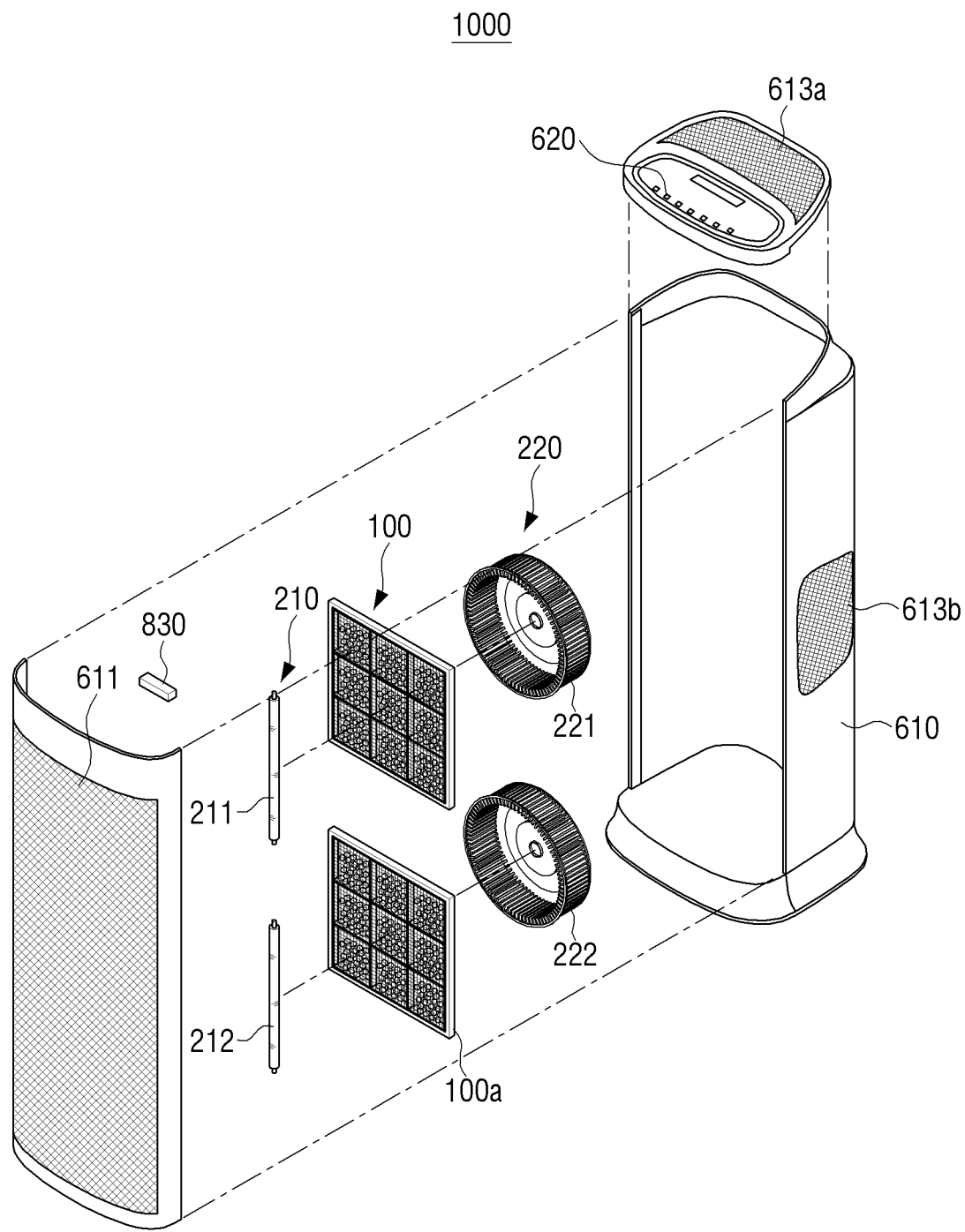
FIG. 15A is an exploded perspective view illustrating an air conditioner according to another exemplary embodiment of the present disclosure.

FIG. 15A is a schematic exploded perspective view illustrating an air conditioner 1000 according to another exemplary embodiment of the present disclosure.

Referring to FIG. 15A, the air conditioner 1000 includes a first photocatalyst filter 100 and a second photocatalyst filter 100a, and the fan unit 220 includes a first fan 221 disposed at a position corresponding to the position of the first photocatalyst filter 100 and a second fan 222 disposed at a position corresponding to the position of the second photocatalyst filter 100a. In addition, the air conditioner 1000 may include a sensor 830 sensing harmful materials.

Photocatalyst beads included in the first photocatalyst filter 100 and photocatalyst beads included in the second photocatalyst filter 100a may be different from each other in at least one of sizes, shapes, and components.

The first fan 221 introduces air into the first photocatalyst filter 100, and the second fan 222 introduces air into the second photocatalyst filter 100a.

The processor 230 may individually control driving of the first fan 221 and the second fan 222 depending on a result sensed by the sensor 830.

Figure 15B:
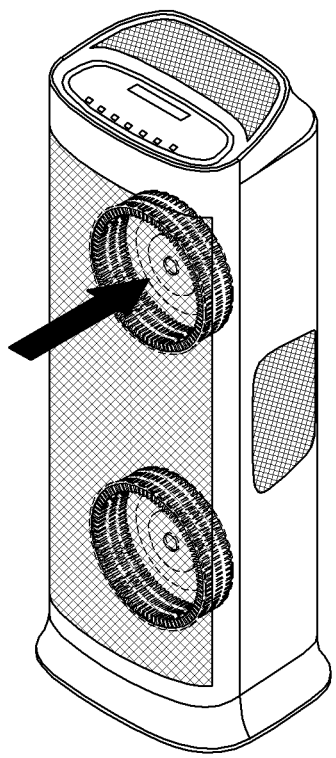
FIGS. 15B and 15C are views for describing an air flow control in the air conditioner according to diverse exemplary embodiments of the present disclosure.
Figure 15C:
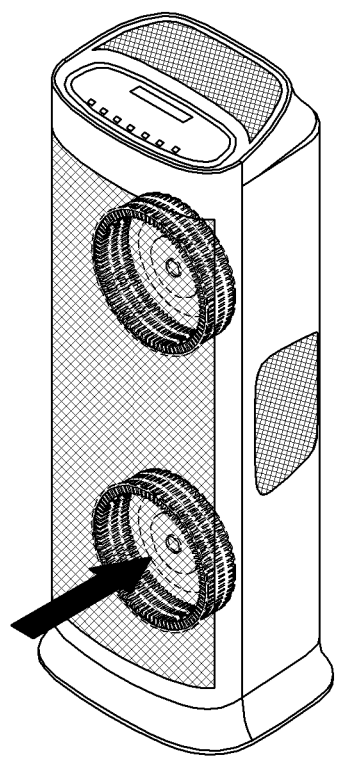

For example, in a case in which the processor 230 drives only the first fan 221 of the first fan 221 and the second fan 222, air may pass through only a place in which the first photocatalyst filter 100 is disposed, as illustrated in FIG. 15B. Alternatively, in a case in which the processor 230 drives only the second fan 222 of the first fan 221 and the second fan 222, air may pass through only a place in which the second photocatalyst filter 100a is disposed, as illustrated in FIG. 15C.

For example, it may be good to use the first photocatalyst filter 100 when an air quality is very bad, but the first photocatalyst filter 100 has a slow filtering speed, and the second photocatalyst filter 100a has a filtering speed faster than that of the first photocatalyst filter 100, but has filtering performance worse than that of the first photocatalyst filter 100. In this case, when the air quality is not very bad, it would be preferable to use only the second photocatalyst filter 100a to increase a lifespan of the first photocatalyst filter 100. There is a case in which it would be preferable to use only any one of the first photocatalyst filter 100 and the second photocatalyst filter 100a.

Therefore, the processor 230 may individually control the driving of the first fan 221 and the second fan 222 on the basis of the result sensed by the sensor 830 to allow the air to pass through only the first photocatalyst filter 100 in a specific situation and allow the air to pass through only the second photocatalyst filter 100a in another situation. The processor 230 may simultaneously drive the first fan 221 and the second fan 222 to allow the air to pass through both of the first photocatalyst filter 100 and the second photocatalyst filter 100a.

A manner of individually driving the first fan 221 and the second fan 222 to allow only the first photocatalyst filter 100 to be used or allow only the second photocatalyst filter 100a to be used as in the exemplary embodiment described above may be used, but the same effect may be obtained by controlling the light source unit 210.

In detail, as illustrated in FIG. 15A, the light source unit 210 may include a first light source 211 and a second light source 212. The processor 230 may individually control the first light source 211 and the second light source 212 on the basis of the result sensed by the sensor 830.

Even in a situation in which the air passes through both of the first photocatalyst filter 100 and the second photocatalyst filter 100a, in a case in which the processor 230 turns on only the first light source 211 of the first light source 211 and the second light source 212, light of the first light source 211 arrives at the second photocatalyst filter 100a to some degree, but only the first photocatalyst filter 100 is mainly activated, such that an effect of using only the first photocatalyst filter 100 of the first photocatalyst filter 100 and the second photocatalyst filter 100a may be obtained. Likewise, in a case in which the processor 230 turns on only the second light source 212 of the first light source 211 and the second light source 212, light of the second light source 212 arrives at the first photocatalyst filter 100 to some degree, but only the second photocatalyst filter 100a is mainly activated, such that an effect of using only the second photocatalyst filter 100a of the first photocatalyst filter 100 and the second photocatalyst filter 100a may be obtained. The processor 230 may simultaneously turn on the first light source 211 and the second light source 212 to activate both of the first photocatalyst filter 100 and the second photocatalyst filter 100a.

Although a case in which the number of light sources corresponds to the number of photocatalyst filters is illustrated in FIG. 15A, the light source unit 210 may include one light source, and a direction of light emitted from one light source may be adjusted by using, for example, the MEMS mirrors, or the like. Although a case in which the number of the photocatalyst filters and the number of the fans are two is illustrated in FIG. 15A, the numbers of the photocatalyst filters and the fans are not limited thereto, but may be various numbers.

According to the diverse exemplary embodiments described above, light efficiency in the photocatalyst filters may be increased, and the channels of the air may be controlled or the photocatalyst filters may be selectively used depending on the air quality, such that filtering efficiency may be increased.

According to another exemplary embodiment of the present disclosure, the air conditioner 1000 may transmit information on several operations performed in the air conditioners 1000 to a server, and the server may transmit control information for automatically controlling the air conditioner 1000 to the air conditioner 1000 or may transmit managing information related to air purification to the user terminal apparatus outside the air conditioner 1000, on the basis of the received information on the several operations. The air conditioner 1000 receiving the control information may perform an operation corresponding to the control information, and the user terminal apparatus receiving the managing information may output information corresponding to the managing information. The present exemplary embodiment will hereinafter be described with reference to FIGS. 26 and 27.

FIG. 26 is a view for describing a managing manner based on operation information of an air conditioner 1000 according to an exemplary embodiment of the present disclosure.

Referring to FIG. 26, a server 300 may be implemented by a cloud server, an Internet hub apparatus, a gateway apparatus, or the like, using cloud computing technology, and a user terminal apparatus 400 may be implemented by an electronic apparatus such as a smart phone, a television (TV), a tablet PC, or the like.

The air conditioner 1000 and the server 300, the server 300 and the user terminal apparatus 400, and the user terminal apparatus 400 and the air conditioner 1000 may communicate with each other through, for example, a local area network (LAN) and an Internet network, or may communicate with each other in a wireless communication manner (for example, Z-wave, 4LoWPAN, RFID, LTE D2D, BLE, GPRS, Weightless, ZigBee, Edge ZigBee, ANT+, NFC, IrDA, DECT, WLAN, Bluetooth, WiFi, WiFi direct, GSM, UMTS, LTE, WiBRO, Cellular (3/4/5G), ultrasonic wave, or the like).

The air conditioner 1000 may perform an operation associated with air conditioning (S2600), and transmit information on the operation to the server 300 (S2610). As an example, the air conditioner 1000 may perform an operation of sensing an air quality through a sensor provided in the air conditioner 1000, and transmit sensed information to the server 300. As another example, the air conditioner 1000 may transmit information on a purifying operation performed in the air conditioner 1000 (for example, information on whether or not a fine dust purifying mode is performed, whether or not a deodorizing mode is performed, which photocatalyst filter is operated, or the like) to the server 300.

The server 300 may analyze the information on the operation received from the air conditioner 1000 (S2620), transmit managing information to the user terminal apparatus 400 (S2630), and the user terminal apparatus 400 may output the managing information (S2635).

Alternatively, the server 300 may receive the information on the operation from the air conditioner 1000 and analyze the information (S2620), and transmit control information for automatically controlling the air conditioner to the air conditioner (S2640), and the air conditioner 1000 may perform an operation corresponding to the received control information (S2645).

According to an exemplary embodiment, the server 300 may provide managing information appropriate for managing a current air quality to the user terminal apparatus 400 on the basis of the sensed information received from the air conditioner 1000. As an example, when it is decided that a concentration of carbon dioxide is increased to a predetermined amount or more on the basis of the sensed information received from the air conditioner 1000, the server 300 may transmit managing information related to the increased concentration of carbon dioxide to the user terminal apparatus 400, and the user terminal apparatus 400 may output a text "A concentration of carbon dioxide in the interior is high. Open windows to ventilate a room." through a display. Alternatively, the server 300 may transmit control information, for allowing an operation for removing carbon dioxide to be performed, to the air conditioner 1000, and the air conditioner 1000 may be automatically switched into an operation mode for removing the carbon dioxide on the basis of the control information. Alternatively, the user terminal apparatus 400 may output a UI screen inquiring whether or not to operate the air conditioner in a carbon dioxide removing mode on the basis of the managing information received from the server 300, and the user terminal apparatus 400 may transmit control signal for a corresponding control to the air conditioner 1000 when user's agreement is input on the UI screen.

As another example, the server 300 may accumulate the sensed information received from the air conditioner 1000, figure out air quality characteristics of a space in which the air conditioner 1000 is disposed on the basis of the accumulated sensed information, and provide customized managing information on the basis of the air quality characteristics. For example, the server 300 may decide air qualities of the space in which the air conditioner 1000 is disposed, in each time zone, on the basis of the sensed information received from the air conditioner 1000 for a predetermined period. In addition, the server 300 may provide managing information in each time zone to the user terminal apparatus 400. For example, when a tendency toward an increase in a pollution level between 2 p.m. and 4 p.m. is analyzed from the sensed information provided from the air conditioner 1000, the server 300 may provide managing information corresponding to such an analysis to the user terminal apparatus 400, and the user terminal apparatus 400 may output a guide text such as "a pollution level is high between 2 p.m. and 4 p.m." through a display. Such a guide text may be provided in a corresponding time or be provided in advance. Alternatively, the server 300 may transmit control information for allowing the air conditioner 1000 to perform an air purifying operation between 2 p.m. and 4 p.m. to the air conditioner 1000, and the air conditioner 1000 may automatically perform the air purifying operation between 2 p.m. and 4 p.m. on the basis of the control information.

As another example, the server 300 may accumulate purifying operation information received from the air conditioner 1000, and determine a use pattern of the air conditioner 1000 of the user on the basis of the accumulated information. For example, a predetermined use pattern of the user operating the air conditioner 1000 in a deodorizing mode between 8 p.m. and 9 p.m. is analyzed as an analysis result of the server 300, the server 300 may transmit control information, for allowing the air conditioner 1000 to be automatically operated in the deodorizing mode between 8 p.m. to 9 p.m., to the air conditioner 1000.

Although a case in which the server 300 is connected to one air conditioner is described in FIG. 26, the server 300 may also be connected to several air conditioners. For example, as illustrated in FIG. 27, the server 300 may be connected to air conditioners 1000-1, 1000-2, and 1000-3 installed in each room. In addition, the server 300 may transmit control information for controlling each of the air conditioners 1000-1, 1000-2, and 1000-3 to each of the air conditioners 1000-1, 1000-2, and 1000-3 on the basis of operation information received from the air conditioners 1000-1, 1000-2, and 1000-3. Alternatively, the server 300 may provide synthetic managing information to the user terminal apparatus 400 on the basis of the operation information received from the air conditioners 1000-1, 1000-2, and 1000-3.

For example, when a tendency toward an increase in a pollution level between 2 p.m. and 4 p.m. is observed in the air conditioner 1000-1 disposed in a first room on the basis of the operation information received from the air conditioners 1000-1, 1000-2, and 1000-3, the server 300 may transmit managing information on such a tendency to the user terminal apparatus 400, and the user terminal apparatus 400 may output a text such as "a pollution level is high in ROOM 1 between 2 p.m. and 4 p.m." as illustrated in FIG. 27.

Alternatively, the server 300 may synthesize the operation information received from the air conditioners 1000-1, 1000-2, and 1000-3 and provide the synthesized information to the user terminal apparatus 400, and the user terminal apparatus 400 may confirm a current state of each of the air conditioners 1000-1, 1000-2, and 1000-3.

As another example, when the server 300 synthesizes sensed information received from the air conditioners 1000-1, 1000-2, and 1000-3 to decide that an air quality is a predetermined pollution level or less, the server 300 may transmit control information for operating only any one of the air conditioners 1000-1, 1000-2, and 1000-3 and turning off the others of the air conditioners 1000-1, 1000-2, and 1000-3 to the air conditioners 1000-1, 1000-2, and 1000-3. Therefore, power consumption may be reduced.

The server 300 may also be connected to other home appliances that may perform communication in the home as well as the air conditioners. As an example, the server 300 may be connected to a robot cleaner, and may transmit control information for allowing the air conditioners 1000-1, 1000-2, and 1000-3 to perform an air cleaning operation to the air conditioners 1000-1, 1000-2, and 1000-3 since generation of dust is expected when it is sensed that the robot cleaner is operated. As another example, the server 300 may be connected to a cooktop disposed in a space in which a first air conditioner 1000-1 is disposed, and may transmit control information for allowing the first air conditioner 1000-1 to be operated in a deodorizing mode to the first air conditioner 1000-1 when it is sensed that cooking is performed in the cooktop.

In addition to the examples described above, the server 300 may provide various information to the user on the basis of the information provided from the air conditioners. In addition, although a case in which the server 300 is disposed in one home is described with reference to FIG. 27, the server 300 may be a synthetic server managing air conditioners of several homes, according to another exemplary embodiment. In this case, the server 300 may collect operation information from the air conditioners in the several homes to build up big data, and may provide more appropriate managing information or control information on the basis of the big data.

According to the exemplary embodiments described above, information on use patterns of the user using the air conditioner 1000 and operation histories of the air conditioner 1000 may be collected, and the air quality may be appropriately managed on the basis of the collected information.

Computer instructions for performing processing operations in the air conditioner 1000, the server 300, or the user terminal apparatus 400 may be stored in a non-transitory computer-readable medium. The computer instructions stored in the non-transitory computer-readable medium allow a specific device to perform the processing operations according to the diverse exemplary embodiments described above when they are executed by a processor of the specific device.

The non-transitory computer-readable medium is not a medium that stores data therein for a while, such as a register, a cache, a memory, or the like, but means a medium that semi-permanently stores data therein and is readable by a device. A specific example of the non-transitory computer-readable medium may include a compact disk (CD), a digital versatile disk (DVD), a hard disk, a Blu-ray disk, a universal serial bus (USB), a memory card, a read only memory (ROM), or the like.

Although exemplary embodiments of the present disclosure have been illustrated and described hereinabove, the present disclosure is not limited to the abovementioned specific exemplary embodiments, but may be variously modified by those skilled in the art to which the present disclosure pertains without departing from the gist of the present disclosure as disclosed in the accompanying claims. These modifications should also be understood to fall within the scope and spirit of the present disclosure.

What is claimed is:

1. A photocatalyst filter comprising:
a base comprising an internal space which is permeable to a fluid;
a plurality of photocatalyst beads provided within the internal space; and
a cover attached to the base,
wherein a surface of the internal space is reflective, and
wherein the cover includes a photocatalyst material.

2. The photocatalyst filter as claimed in claim 1, wherein the base further comprises a plurality of reflective walls defining the internal space.

3. The photocatalyst filter as claimed in claim 2, wherein the plurality of walls are formed of a reflective material.

4. The photocatalyst filter as claimed in claim 3, wherein the reflective material is one of a metal and a light-reflective resin.

5. The photocatalyst filter as claimed in claim 1, wherein the plurality of photocatalyst beads comprise a photocatalyst material and an adsorbent.

6. The photocatalyst filter as claimed in claim 5, wherein the adsorbent is at least one of activated carbon and zeolite.

7. The photocatalyst filter as claimed in claim 1, wherein the plurality of photocatalyst beads have spherical shapes that are hollow.

8. The photocatalyst filter as claimed in claim 1, wherein the plurality of photocatalyst beads have protrusions formed on surfaces thereof.

9. The photocatalyst filter as claimed in claim 1, wherein the cover retains the photocatalyst beads within the internal space.

10. An air conditioner comprising:
a photocatalyst filter comprising a base comprising an internal space through which is permeable to a fluid and a plurality of photocatalyst beads provided within the internal space, wherein a surface of the internal space is reflective;
a fan unit configured to introduce air into the photocatalyst filter;
a light source unit configured to irradiate light onto the photocatalyst filter; and
a processor configured to control the fan unit and the light source unit,
wherein the photocatalyst filter comprises a first photocatalyst filter and a second photocatalyst filter,
wherein the fan unit comprises:
a first fan configured to introduce air into the first photocatalyst filter; and
a second fan configured to introduce air into the second photocatalyst filter.

11. The air conditioner as claimed in claim 10, wherein the first photocatalyst filter comprises first photocatalyst beads and the second photocatalyst filter comprises second photocatalyst beads, and wherein at least one of sizes, shapes, and components of the first photocatalyst beads are different from a corresponding at least one of sizes, shapes, and components of the second photocatalyst beads.

12. The air conditioner as claimed in claim 10, further comprising a sensor configured to sense a harmful material,
wherein the processor is configured to individually control the first fan and the second fan depending on a result sensed by the sensor.

13. The air conditioner as claimed in claim 10, wherein the photocatalyst filter comprises a first photocatalyst filter and a second photocatalyst filter,
wherein the light source unit comprises:
a first light source configured to irradiate light onto the first photocatalyst filter; and
a second light source configured to irradiate light onto the second photocatalyst filter.

14. The air conditioner as claimed in claim 13, further comprising a sensor configured to sense a harmful material,
wherein the processor is configured to individually control the first light source and the second light source depending on a result sensed by the sensor.

* * * * *